(12) United States Patent
Kodama et al.

(10) Patent No.: US 10,087,263 B2
(45) Date of Patent: Oct. 2, 2018

(54) CURABLE COMPOSITION, POLYMER FUNCTIONAL CURED PRODUCT, WATER-SOLUBLE ACRYLAMIDE COMPOUND, AND METHOD FOR MANUFACTURING SAME

(71) Applicant: FUJIFILM Corporation, Tokyo (JP)

(72) Inventors: Keisuke Kodama, Kanagawa (JP); Kuniyuki Kaminaga, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/252,859

(22) Filed: Aug. 31, 2016

(65) Prior Publication Data

US 2016/0369017 A1 Dec. 22, 2016

Related U.S. Application Data

(63) Continuation of application No. PCT/JP2015/055409, filed on Feb. 25, 2015.

(30) Foreign Application Priority Data

Mar. 12, 2014 (JP) .................................. 2014-049187

(51) Int. Cl.
*C08F 20/58* (2006.01)
*B01J 39/20* (2006.01)
(Continued)

(52) U.S. Cl.
CPC .......... *C08F 20/58* (2013.01); *B01D 67/0006* (2013.01); *B01D 71/40* (2013.01);
(Continued)

(58) Field of Classification Search
USPC ........................................................ 521/27
See application file for complete search history.

(56) References Cited

U.S. PATENT DOCUMENTS 4,034,001 A * 7/1977 Miller .................... C08F 20/60
508/404
4,876,047 A * 10/1989 Benn ..................... C07C 309/15
562/105

FOREIGN PATENT DOCUMENTS

JP         61-47458 A    3/1986
JP        61-212550 A    9/1986
(Continued)

OTHER PUBLICATIONS

International Search Report for PCT/JP2015/055409 dated May 26, 2015 [PCT/ISA/210].
(Continued)

*Primary Examiner* — Mark Kaucher
*Assistant Examiner* — Henry Hu
(74) *Attorney, Agent, or Firm* — Sughrue Mion, PLLC

(57) ABSTRACT

There is provided a curable composition including a water-soluble acrylamide monomer represented by the following General Formula (1-1) or (1-2), a polymer functional cured product, a water-soluble acrylamide compound, and a method for manufacturing the same.

General Formula (1-1)

General Formula (1-2)

(Continued)

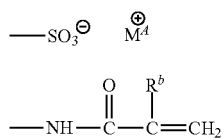

General Formula (a)

General Formula (b)

In General Formulas (1-1) and (1-2), m represents an integer of 2 or greater, and L represents an m-valent group or a single bond. Here, in a case where L is a single bond, m is 2. $L^1$ and $L^2$ each represent a single bond or a divalent linking group. $R^1$ to $R^5$ each represent a hydrogen atom or a substituent, and may be bonded to each other to form a ring, and may be bonded to L, $L^1$, or $L^2$ to form a ring. Either one of $R^A$ and $R^B$ represents a group represented by General Formula (a), and the other represents a group represented by General Formula (b).

14 Claims, 1 Drawing Sheet

(51) Int. Cl.
| | |
|---|---|
| *B01D 71/40* | (2006.01) |
| *C07C 309/24* | (2006.01) |
| *B01D 71/82* | (2006.01) |
| *C08F 222/38* | (2006.01) |
| *H01B 1/12* | (2006.01) |
| *H01M 8/1023* | (2016.01) |
| *H01M 8/1069* | (2016.01) |
| *H01M 8/1072* | (2016.01) |
| *B01D 67/00* | (2006.01) |
| *C07C 303/32* | (2006.01) |
| *C08J 5/22* | (2006.01) |
| *B01D 61/00* | (2006.01) |
| *B01D 61/02* | (2006.01) |
| *B01D 61/42* | (2006.01) |

(52) U.S. Cl.
CPC .............. *B01D 71/82* (2013.01); *B01J 39/20* (2013.01); *C07C 303/32* (2013.01); *C07C 309/24* (2013.01); *C08F 222/38* (2013.01); *C08J 5/2231* (2013.01); *H01B 1/122* (2013.01); *H01M 8/1023* (2013.01); *H01M 8/1069* (2013.01); *H01M 8/1072* (2013.01); *B01D 61/002* (2013.01); *B01D 61/025* (2013.01); *B01D 61/42* (2013.01); *B01D 2323/30* (2013.01); *B01D 2323/345* (2013.01); *B01D 2325/14* (2013.01); *B01D 2325/26* (2013.01); *C08J 2333/24* (2013.01); *Y02P 70/56* (2015.11)

(56) References Cited

FOREIGN PATENT DOCUMENTS

| | | |
|---|---|---|
| JP | 2007-146108 A | 6/2007 |
| JP | 2012-153853 A | 8/2012 |
| JP | 2014-195798 A | 10/2014 |
| WO | 2013/011272 A1 | 1/2013 |
| WO | 2013/011273 A1 | 1/2013 |
| WO | WO-2013/011272 A1 * | 1/2013 |
| WO | WO-2013/011273 A1 * | 1/2013 |

OTHER PUBLICATIONS

Communication dated Dec. 12, 2017 from the State Intellectual Property Office of the P.R.C. in counterpart Chinese application No. 201580012740.X.

* cited by examiner

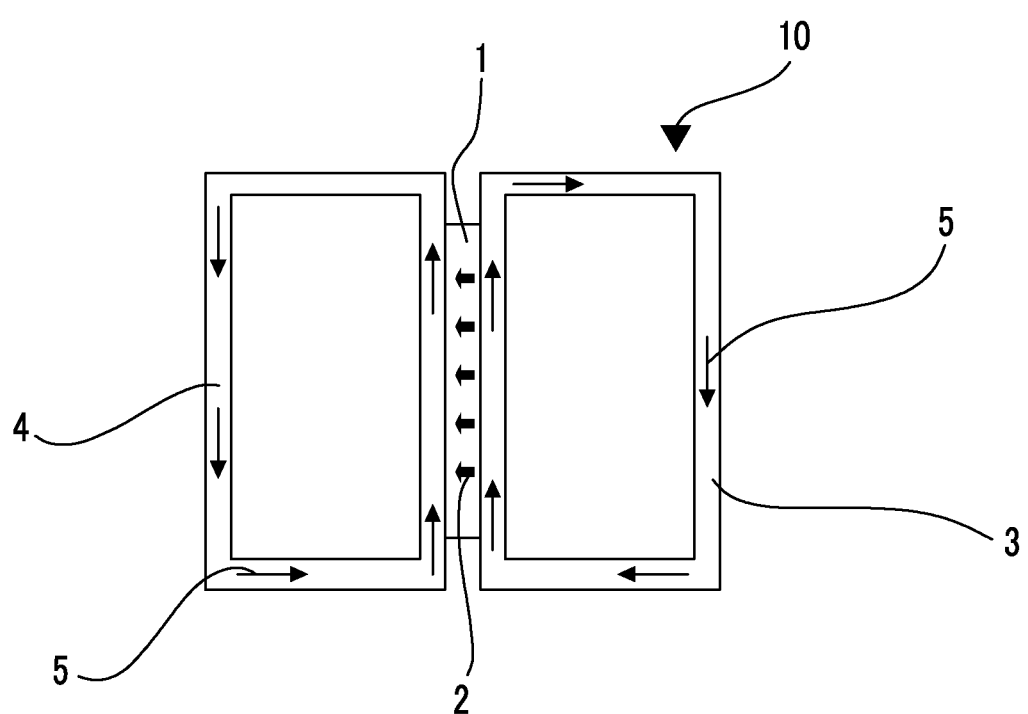

CURABLE COMPOSITION, POLYMER FUNCTIONAL CURED PRODUCT, WATER-SOLUBLE ACRYLAMIDE COMPOUND, AND METHOD FOR MANUFACTURING SAME

CROSS-REFERENCE TO RELATED APPLICATIONS

This application is a Continuation of PCT International Application No. PCT/JP2015/055409 filed on Feb. 25, 2015, which claims priority under 35 U.S.C. § 119 (a) to Japanese Patent Application No. 2014-049187 filed in Japan on Mar. 12, 2014. Each of the above applications is hereby expressly incorporated by reference, in its entirety, into the present application.

BACKGROUND OF THE INVENTION

1. Field of the Invention

The present invention relates to a curable composition, a polymer functional cured product, a water-soluble acrylamide compound, and a method for manufacturing the same.

2. Description of the Related Art

Ion-exchange membranes are used in electrodeionization (EDI), continuous electrodeionization (CEDI), electrodialysis (ED), and electrodialysis reversal (EDR). In addition, ion-exchange membranes are used in not only general applications but also medical applications, and in recent years, have been used in a solid polymer electrolyte type fuel cell.

Here, electrodeionization (EDI) is a water treatment process in which ions are removed from an aqueous liquid using an ion-exchange membrane and a potential to achieve ion transport. Unlike other water purification techniques for ion-exchange in the related art, electrodeionization (EDI) does not require the use of chemicals such as acids or caustic soda, and can be used to produce ultrapure water. Electrodialysis (ED) and electrodialysis reversal (EDR) are electrochemical separation processes in which ions or the like are removed from water or other fluids.

Regarding ion-exchange membranes, there is an anion-exchange membrane having a cationic group such as quaternary ammonium (for example, refer to WO2013/011273A) and a cation-exchange membrane having an anionic group such as sulfonate (for example, refer to WO2013/011272A), mainly in the polymer, and research on improvement thereof has been actively performed on both. In addition, although not an ion-exchange membrane, bis-amidealkyl sulfonic acid is also known (refer to U.S. Pat. No. 4,034,001A).

SUMMARY OF THE INVENTION

Low water permeability, low electric resistance, and high ion selectivity which are the main performance for an ion-exchange membrane (hereinafter, also simply referred to as a "membrane") are significantly influenced by the ion-exchange capacity, the crosslink density, and the pore size of the membrane.

In the studies so far of the present inventors, it was found that as the solution concentration at the time of applying and curing an ionic monomer and a cross-linking monomer is increased, the pore size is reduced, and the ion-exchange membrane performance is improved.

However, commercially available acrylamide crosslinking agents have low water-solubility, and due to this, it is difficult to apply at a high concentration.

In contrast, by using a monomer (charged crosslinker) having both an ionic group and a cross-linking group, the water-solubility of the monomer is improved, and application at a high concentration becomes possible. Furthermore, it was found that by improvement of the ion-exchange capacity and the crosslink density, the ion-exchange membrane performance is significantly improved.

However, among the monomers having both an ionic group and a cross-linking group, a monomer for a cation-exchange membrane is complicated in terms of synthesis, and the cost thereof is high. In addition, for an aromatic sulfonic acid monomer generally used, it is difficult to introduce two or more sulfonic acids into one aromatic ring, and due to this, there is an upper limit on the ion-exchange capacity and the crosslink density, and there is also a limit on the ion-exchange membrane performance.

Accordingly, an object of the present invention is to provide a curable composition which has excellent performance as an ion-exchange membrane, particularly, a cation-exchange membrane and can be manufactured efficiently and at a low cost, a polymer functional cured product, a water-soluble acrylamide compound, and a method for manufacturing the same.

In particular, an object of the present invention is to provide a curable composition which has low electric resistance and water permeability for a membrane, among the performances of an ion-exchange membrane, and has high permselectivity (transport number), a polymer functional cured product, a water-soluble acrylamide compound, and a method for manufacturing the same.

The present inventors thought that development of a water-soluble acrylamide monomer (compound) having a plurality of sulfo groups and acrylamide groups was important, and as a result of various studies thereon, they found a new water-soluble acrylamide monomer (compound), and found that the above object can be achieved.

The present invention has been completed based on these findings.

<1> A curable composition comprising a water-soluble acrylamide monomer represented by the following General Formula (1-1) or (1-2).

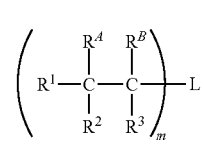

General Formula (1-1)

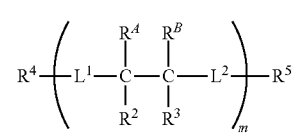

General Formula (1-2)

In General Formulas (1-1) and (1-2), m represents an integer of 2 or greater, and L represents an m-valent group or a single bond. Here, in a case where L is a single bond, m is 2. $L^1$ and $L^2$ each independently represent a single bond or a divalent linking group. $R^1$ to $R^5$ each independently represent a hydrogen atom or a substituent, and may be bonded to each other to form a ring, and may be bonded to L, $L^1$, or $L^2$ to form a ring. Either one of $R^A$ and $R^B$ represents a group represented by the following General Formula (a), and the other represents a group represented by the following General Formula (b). Here, m —[C($R^3$)($R^B$)—C($R^1$)($R^2$)($R^4$)]'s may be the same as or different from each other, m -[$L^2$-C($R^3$)($R^B$)—C($R^2$)($R^4$)-$L^1$]-'s may be the same as or different from each other, and in m —[C($R^3$)($R^B$)—C($R^1$)($R^2$)($R^4$)]'s or m -[$L^2$-C($R^3$)($R^B$)—C($R^2$)($R^4$)-$L^1$]-'s, $R^A$ or $R^B$ may be substituted with the group represented by the following General Formula (a).

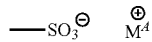

General Formula (a)

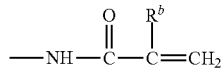

General Formula (b)

In General Formula (a), $M^A$ represents a hydrogen ion, an inorganic ion, or an organic ion. Here, each of the inorganic ion and the organic ion may be a di- or higher valent ion.

In General Formula (b), $R^b$ represents a hydrogen atom or an alkyl group.

<2> The curable composition according to <1>, in which m is 2, and L is a single bond, an alkylene group, or an arylene group.

<3> The curable composition according to <1> or <2>, in which the water-soluble acrylamide monomer represented by General Formula (1-1) is represented by the following General Formula (2).

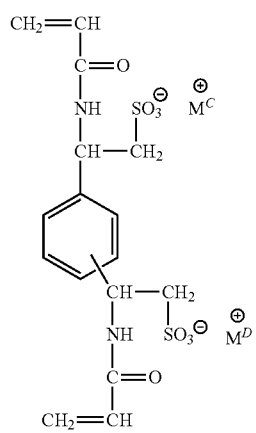

General Formula (2)

In General Formula (2), $M^C$ and $M^D$ each independently represent a hydrogen ion, an inorganic ion, or an organic ion. Here, each of the inorganic ion and the organic ion may be a di- or higher valent ion.

<4> A polymer functional cured product which is formed by polymerizing and curing the curable composition according to any one of <1> to <3>.

<5> A polymer functional cured product comprising a polymer having a structural unit represented by General Formula (I-1) or (I-2).

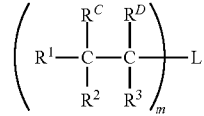

General Formula (1-1)

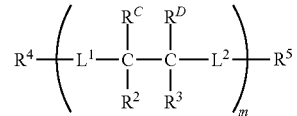

General Formula (1-2)

In General Formulas (I-1) and (I-2), m represents an integer of 2 or greater, and L represents an m-valent group or a single bond. Here, in a case where L is a single bond, m is 2. $L^1$ and $L^2$ each independently represent a single bond or a divalent linking group. $R^1$ to $R^5$ each independently represent a hydrogen atom or a substituent, and may be bonded to each other to form a ring or may be bonded to L, $L^1$, or $L^2$ to form a ring. Either one of $R^C$ and $R^D$ represents a group represented by the following General Formula (a), and the other represents a group represented by the following General Formula (c). Here, m —[C($R^3$)($R^D$)—C($R^1$)($R^2$)($R^C$)]'s may be the same as or different from each other, m -[$L^2$-C($R^3$)($R^D$)—C($R^2$)($R^C$)-$L^1$]-'s may be the same as or different from each other, and in m —[C($R^3$)($R^D$)—C($R^1$)($R^2$)($R^C$)]'s or m -[$L^2$-C($R^3$)($R^D$)—C($R^2$)($R^C$)-$L^1$]-'s, $R^C$ or $R^D$ may be substituted with the group represented by the following General Formula (a).

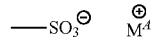

General Formula (a)

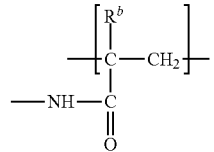

General Formula (c)

In General Formula (a), $M^A$ represents a hydrogen ion, an inorganic ion, or an organic ion. Here, each of the inorganic ion and the organic ion may be a di- or higher valent ion.

In General Formula (c), $R^b$ represents a hydrogen atom or an alkyl group.

<6> The polymer functional cured product according to <5>, in which m is 2, and L is a single bond, an alkylene group, or an arylene group.

<7> The polymer functional cured product according to <5> or <6>, in which the structural unit represented by General Formula (I-1) is a structural unit represented by the following General Formula (II).

General Formula (II)

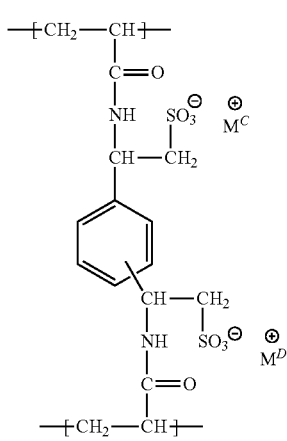

In General Formula (II), $M^C$ and $M^D$ each independently represent a hydrogen ion, an inorganic ion, or an organic ion. Here, each of the inorganic ion and the organic ion may be a di- or higher valent ion.

<8> The polymer functional cured product according to any one of <4> to <7>, in which the polymer functional cured product is an ion-exchange membrane, a proton conductive membrane, a reverse osmosis membrane, a forward osmosis membrane, a polymer electrolyte, or a water-absorbing resin.

<9> A water-soluble acrylamide compound represented by the following General Formula (1-1) or (1-2).

General Formula (1-1)

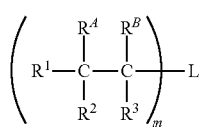

General Formula (1-2)

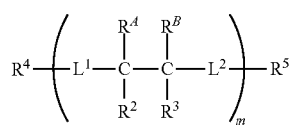

In General Formulas (1-1) and (1-2), m represents an integer of 2 or greater, and L represents an m-valent group or a single bond. Here, in a case where L is a single bond, m is 2. $L^1$ and $L^2$ each independently represent a single bond or a divalent linking group. $R^1$ to $R^5$ each independently represent a hydrogen atom or a substituent, and may be bonded to each other to form a ring or may be bonded to L, $L^1$, or $L^2$ to form a ring. Either one of $R^A$ and $R^B$ represents a group represented by the following General Formula (a), and the other represents a group represented by the following General Formula (b). Here, m —[C($R^3$)($R^B$)—C($R^1$)($R^2$)($R^A$)]'s may be the same as or different from each other, m -[$L^2$-C($R^3$)($R^B$)—C($R^2$)($R^A$)-$L^1$]-'s may be the same as or different from each other, and in m —[C($R^3$)($R^B$)—C($R^1$)($R^2$)($R^A$)]'s or m -[$L^2$-C($R^3$)($R^B$)—C($R^2$)($R^A$)-$L^1$]-'s, $R^A$ or $R^B$ may be substituted with the group represented by the following General Formula (a).

General Formula (a)

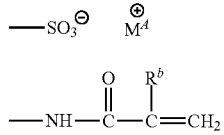

General Formula (b)

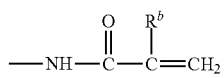

In General Formula (a), $M^A$ represents a hydrogen ion, an inorganic ion, or an organic ion. Here, each of the inorganic ion and the organic ion may be a di- or higher valent ion.

In General Formula (b), $R^b$ represents a hydrogen atom or an alkyl group.

<10> The water-soluble acrylamide compound according to <9>, in which m is 2, and L is a single bond, an alkylene group, or an arylene group.

<11> The water-soluble acrylamide compound according to <9> or <10>, in which the water-soluble acrylamide compound represented by General Formula (1-1) is represented by the following General Formula (2).

General Formula (2)

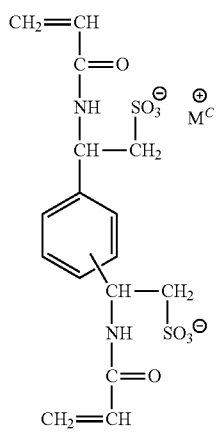

In General Formula (2), $M^C$ and $M^D$ each independently represent a hydrogen ion, an inorganic ion, or an organic ion. Here, each of the inorganic ion and the organic ion may be a di- or higher valent ion.

<12> A method for manufacturing a water-soluble acrylamide compound, in which an olefin compound represented by the following General Formula (3-1) or (3-2), acrylonitrile, and fuming sulfuric acid are reacted.

General Formula (3-1)

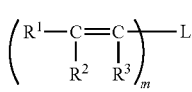

General Formula (3-2)

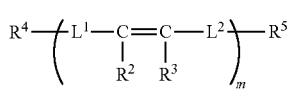

In General Formulas (3-1) and (3-2), m represents an integer of 2 or greater, and L represents an m-valent group or a single bond. Here, in a case where L is a single bond, m is 2. $L^1$ and $L^2$ each independently represent a single bond or a divalent linking group. $R^1$ to $R^5$ each independently represent a hydrogen atom or a substituent, and may be bonded to each other to form a ring or may be bonded to L, $L^1$, or $L^2$ to form a ring. Here, m —[C(R$^3$)═C(R$^1$)(R$^2$)]'s may be the same as or different from each other, and m -[L$^2$-C(R$^3$)═C(R$^2$)-L$^1$]-'s may be the same as or different from each other.

<13> The method for manufacturing a water-soluble acrylamide compound according to <12>, in which m is 2, and L is a single bond, an alkylene group, or an arylene group.

<14> The method for manufacturing a water-soluble acrylamide compound according to <12> or <13>, in which the olefin compound represented by General Formula (3-1) is divinylbenzene.

In the present specification, "to" is used to describe a range in which the numerical values shown before and after "to" indicate the lower limit value and the upper limit value.

In addition, in each general formula, unless specified otherwise, in a case where a plurality of groups having the same sign are present, these may be the same as or different from each other, and in a case where a plurality of repetitions of partial structures are present, these repetitions may be the same repetition or may be a mixture of different repetitions in the range specified.

Furthermore, even in a case where one of isomers is described for convenience of display, unless otherwise specified, the geometric isomer which is a substitution pattern of the double bond in each general formula may be an E isomer or a Z isomer, or may be a mixture thereof.

In the present invention, the term "acryl" includes not only a compound in which a methyl group has been substituted at the α position of an acyl group such as acryl or methacryl but also a compound in which an alkyl group has been substituted, and is used as a collective term for acids or salts thereof, esters, or amides. That is, the term "acryl" includes both acrylic esters, amides, or acids or salts thereof, and α-alkyl substituted acrylic esters, amides, or acids or salts thereof.

According to the present invention, it is possible to provide a curable composition which has excellent performance as an ion-exchange membrane and can be manufactured efficiently and at a low cost, a polymer functional cured product, a water-soluble acrylamide compound, and a method for manufacturing the same.

In particular, it is possible to provide a curable composition which has low electric resistance and water permeability for a membrane, among the performances of the ion-exchange membrane, and has high permselectivity (transport number), a polymer functional cured product, a water-soluble acrylamide compound, and a method for manufacturing the same.

The above-described or other features and advantages of the present invention will become apparent from the following description with reference to the accompanying suitable drawings.

BRIEF DESCRIPTION OF THE DRAWINGS

FIG. 1 is a diagram schematically showing a flow path of a device for measuring water permeability for a membrane.

DESCRIPTION OF THE PREFERRED EMBODIMENTS

<<Curable Composition>>

The curable composition of the present invention includes a water-soluble acrylamide monomer represented by the following General Formula (1-1) or (1-2).

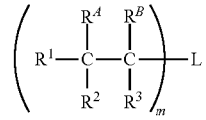

General Formula (1-1)

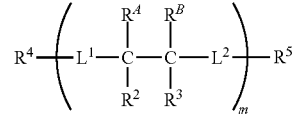

General Formula (1-2)

In General Formulas (1-1) and (1-2), m represents an integer of 2 or greater, and L represents an m-valent group or a single bond. Here, in a case where L is a single bond, m is 2. $L^1$ and $L^2$ each independently represent a single bond or a divalent linking group. $R^1$ to $R^5$ each independently represent a hydrogen atom or a substituent, and these may be bonded to each other to form a ring or may be bonded to L, $L^1$, or $L^2$ to form a ring. Either one of $R^A$ and $R^B$ represents a group represented by the following General Formula (a), and the other represents a group represented by the following General Formula (b). Here, m —[C(R$^3$)(R$^B$)—C(R$^1$)(R$^2$)(R$^A$)]'s may be the same as or different from each other, m -[L$^2$-C(R$^3$)(R$^B$)—C(R$^2$)(R$^A$)-L$^1$]-'s may be the same as or different from each other, and in m —[C(R$^3$)(R$^B$)—C(R$^1$)(R$^2$)(R$^A$)]'s or m -[L$^2$-C(R$^3$)(R$^B$)—C(R$^2$)(R$^A$)-L$^1$]-'s, $R^A$ or $R^B$ may be substituted with the group represented by the following General Formula (a).

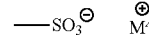

General Formula (a)

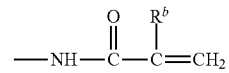

General Formula (b)

In General Formula (a), $M^A$ represents a hydrogen ion, an inorganic ion, or an organic ion. Here, each of the inorganic ion and the organic ion may be a di- or higher valent ion.

In General Formula (b), $R^b$ represents a hydrogen atom or an alkyl group.

Here, the compound represented by General Formula (1-1) or (1-2) is a water-soluble acrylamide monomer and is water-soluble. In the present invention, the "water-soluble" compound means a compound of which 5 g or greater dissolves in 100 ml of water at 25° C., a compound of which 20 g or greater dissolves in 100 ml of water at 25° C. is preferable, and a compound of which 100 g or greater dissolves in 100 ml of water at 25° C. is more preferable.

In the present invention, m is preferably an integer of 2 to 4, more preferably an integer of 2 or 3, and still more preferably is 2.

In the case of a chain hydrocarbon, the m-valent group represented by L preferably has 1 to 20 carbon atoms and more preferably has 1 to 10 carbon atoms, in the case of a cyclic hydrocarbon, the m-valent group represented by L preferably has 3 to 20 carbon atoms and more preferably has 5 to 20 carbon atom, and in the case of an aromatic ring group, the m-valent group represented by L preferably has 6 to 20 carbon atoms and more preferably has 6 to 12 carbon atoms.

In a case where L is a divalent group, a single bond, an alkylene group, or an arylene group is preferable.

The alkylene group preferably has 1 to 20 carbon atoms, more preferably has 1 to 10 carbon atoms, still more preferably has 1 to 3 carbon atoms, and particularly preferably has 1 or 2 carbon atoms, and examples thereof include a methylene group, an ethylene group, a propylene group, and a hexamethylene group.

The arylene group preferably has 6 to 20 carbon atoms and more preferably has 6 to 12 carbon atoms, and examples thereof include a phenylene group and a naphthylene group, and a phenylene group is preferable.

The divalent linking group represented by $L^1$ or $L^2$ is preferably an alkylene group or an arylene group, the preferable range of the alkylene group or the arylene group is the same as that of the alkylene group or the arylene group represented by L described above.

Examples of the substituent represented by each of $R^1$ to $R^5$ include a substituent group α described below, and the substituent is preferably an alkyl group or an aryl group, and more preferably an alkyl group.

Each of $R^1$ to $R^5$ is preferably a hydrogen atom, an alkyl group, or an aryl group, more preferably a hydrogen atom or an alkyl group, and still more preferably a hydrogen atom.

The alkyl group is a linear or branched alkyl group, preferably has 1 to 10 carbon atoms, more preferably has 1 to 5 carbon atoms, still more preferably has 1 to 3 carbon atoms, particularly preferably has 1 or 2 carbon atoms, and most preferably has 1 carbon atom, and examples thereof include a methyl group, an ethyl group, an isopropyl group, an n-octyl group, a 2-ethylhexyl group, and an n-decyl group.

The arylene group preferably has 6 to 20 carbon atoms and more preferably has 6 to 12 carbon atoms, and examples thereof include a phenyl group and a naphthyl group.

In General Formula (1-2), $R^4$ and $R^5$ may be bonded to each other to form a ring, and in this case, the resultant ring compound can be represented by the following General Formula (1-2a).

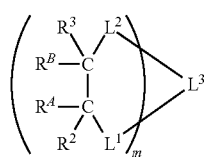

General Formula (1-2a)

In General Formula (1-2a), m, $R^2$, $R^3$, $R^A$, $R^B$, $L^1$, and $L^2$ have the same meaning as m, $R^2$, $R^3$, $R^A$, $R^B$, $L^1$, and $L^2$ in General Formula (1-2), respectively, and the preferable ranges thereof are also the same. $L^3$ represents a single bond or a divalent linking group.

Examples of the divalent linking group represented by $L^3$ include the same as the divalent linking groups represented by $L^1$ or $L^2$, and the preferable range thereof is also the same.

The ring formed by bonding of $R^4$ and $R^5$ to each other is preferably a 5- to 16-membered ring, more preferably a 5- to 14-membered ring, and particularly preferably a 6- to 12-membered ring. In addition, the ring formed is preferably a cycloalkane, and among cycloalkanes, cyclohexane or cyclododecane is preferable.

The inorganic ion represented by $M^A$ is preferably an alkali metal ion. Examples of the alkali metal ion include a lithium ion, a potassium ion, and a sodium ion, and these are preferable.

Examples of the organic ion represented by $M^A$ include a quaternary ammonium ion.

$M^A$ is preferably a hydrogen ion or an inorganic ion and more preferably a hydrogen ion, a lithium ion, a potassium ion, or a sodium ion.

The alkyl group represented by $R^b$ is a linear or branched alkyl group, preferably has 1 to 10 carbon atoms, more preferably has 1 to 5 carbon atoms, still more preferably has 1 to 3 carbon atoms, and particularly preferably has 1 carbon atom, and specific examples of the alkyl group include a methyl group, an ethyl group, an isopropyl group, a t-butyl group, an n-octyl group, a 2-ethylhexyl group, and an n-decyl group.

$R^b$ is preferably a hydrogen atom or a methyl group, and more preferably a hydrogen atom.

In the present invention, the water-soluble acrylamide monomer represented by General Formula (1-1) is preferably a compound represented by the following General Formula (2).

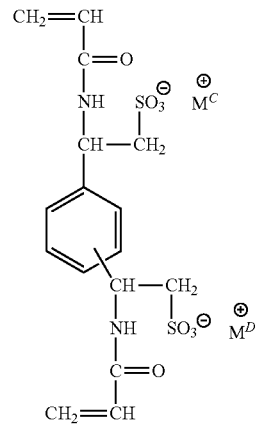

General Formula (2)

In General Formula (2), $M^C$ and $M^D$ have the same meaning as $M^A$ in General Formula (a), respectively, and the preferable ranges thereof are also the same.

Specific examples of the water-soluble acrylamide monomer represented by General Formula (1-1) or (1-2) are shown below, but the present invention is not limited thereto.

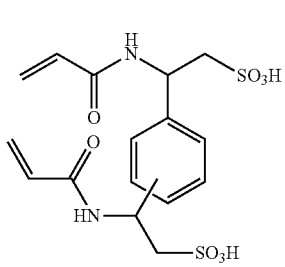 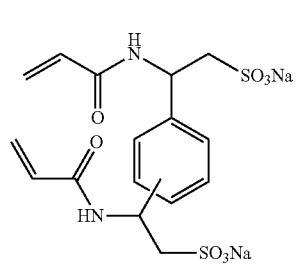 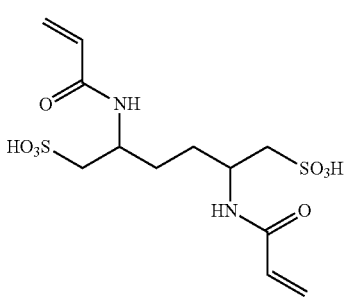

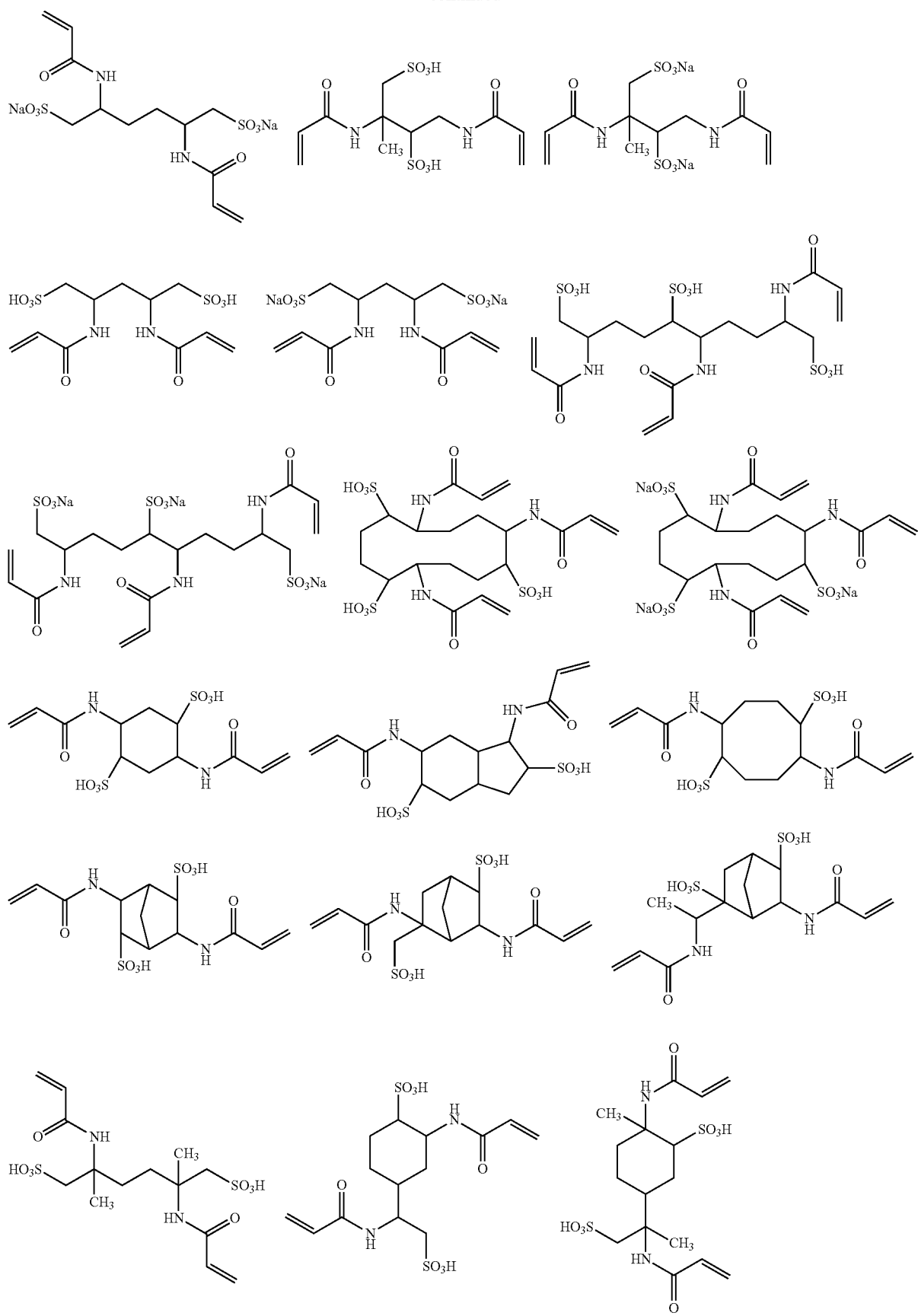

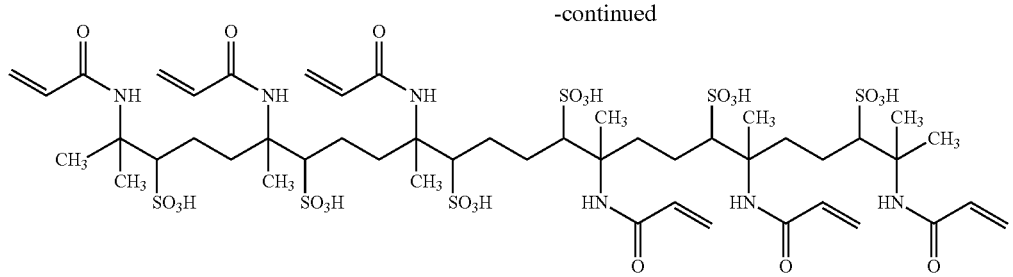

The curable composition of the present invention may include a water-soluble acrylamide monomer represented by the following General Formula (M), in addition to the water-soluble acrylamide monomer represented by General Formula (1-1) or (1-2).

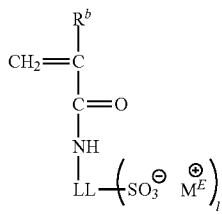

General Formula (M)

In General Formula (M), $R^b$ has the same meaning as $R^b$ in General Formula (b), and the preferable range thereof is also the same. $M^E$ has the same meaning as $M^A$ in General Formula (a), and the preferable range thereof is also the same. LL represents residues obtained by removing one or more hydrogen atoms from an alkyl group or an aryl group, or a combination of these residues, and l represents an integer of 0 to 10.

The alkyl group in LL preferably has 1 to 12 carbon atoms, more preferably has 1 to 8 carbon atoms, and still more preferably has 1 to 4 carbon atoms, and examples thereof include a methyl group, an ethyl group, a propyl group, and a t-butyl group. -LL-$(SO_3^-M^{E+})_l$ is particularly preferably *—$C(CH_3)_2CH_2$—$SO_3^-M^{E+}$. Here, * indicates a position at which the nitrogen atom in amide is bonded.

The aryl group in LL preferably has 6 to 16 carbon atoms and more preferably has 6 to 12 carbon atoms, and examples thereof include a phenyl group and a naphthyl group.

l is preferably 0 to 4, more preferably 1 to 3, and still more preferably 1 or 2.

Specific examples of the water-soluble acrylamide monomer represented by General Formula (M) are shown below, but the present invention is not limited thereto.

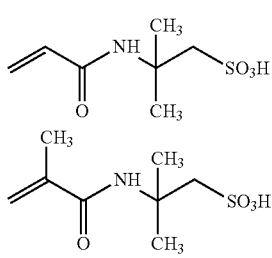

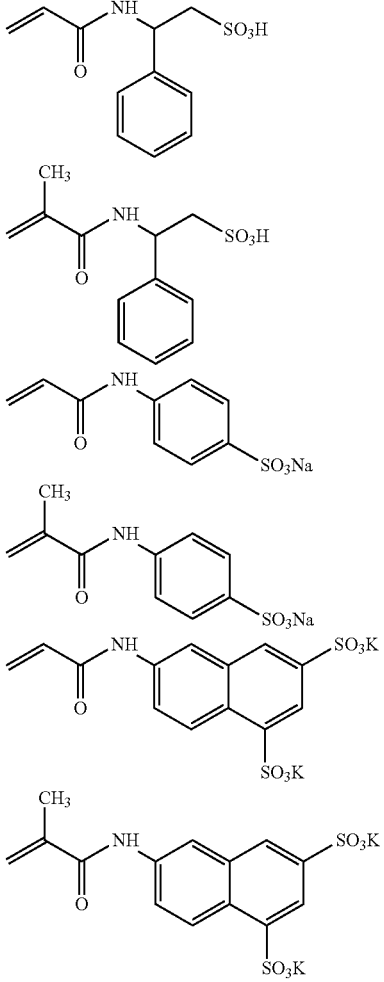

The content of the water-soluble acrylamide monomer represented by General Formula (1-1) or (1-2) in 100 parts by mass of the monomer components to form a curable composition is preferably 10 parts by mass to 100 parts by mass, more preferably 40 parts by mass to 100 parts by mass, still more preferably 60 parts by mass to 100 parts by mass, and particularly preferably 100 parts by mass. The content of the water-soluble acrylamide monomer represented by General Formula (M) is preferably 0 parts by mass to 70 parts by mass, more preferably 0 parts by mass to 60 parts by mass, still more preferably 0 parts by mass to 40 parts by mass, and is particularly preferably not included.

Here, the substituent group α will be described.

The substituent group α is the group of substituents consisting of the following substituents.

(Substituent Group α)

Examples of the substituent group α include an alkyl group (preferably an alkyl group having 1 to 30 carbon atoms, more preferably an alkyl group having 1 to 20 carbon atoms, and particularly preferably an alkyl group having 1 to 10 carbon atoms, and examples thereof include a methyl group, an ethyl group, an isopropyl group, a t-butyl group, an n-octyl group, a 2-ethylhexyl group, an n-decyl group, and an n-hexadecyl group), a cycloalkyl group (preferably a cycloalkyl group having 3 to 30 carbon atoms, more preferably a cycloalkyl group having 3 to 20 carbon atoms, and particularly preferably a cycloalkyl group having 3 to 10 carbon atoms, and examples thereof include a cyclopropyl group, a cyclopentyl group, and a cyclohexyl group), an alkenyl group (preferably an alkenyl group having 2 to 30 carbon atoms, more preferably an alkenyl having 2 to 20 carbon atoms, and particularly preferably an alkenyl group having 2 to 10 carbon atoms, and examples thereof include a vinyl group, an allyl group, a 2-butenyl group, and a 3-pentenyl group), an alkynyl group (preferably an alkynyl group having 2 to 30 carbon atoms, more preferably an alkynyl having 2 to 20 carbon atoms, and particularly preferably an alkynyl group having 2 to 10 carbon atoms, and examples thereof include a propargyl group and a 3-pentynyl group), an aryl group (preferably an aryl group having 6 to 30 carbon atoms, more preferably an aryl having 6 to 20 carbon atoms, and particularly preferably an aryl group having 6 to 12 carbon atoms, and examples thereof include a phenyl group, a p-methylphenyl group, a naphthyl group, and an anthranyl group), an amino group (including an amino group, an alkylamino group, and an arylamino group, preferably an amino group having 0 to 30 carbon atoms, more preferably an amino having 0 to 20 carbon atoms, and particularly preferably an amino group having 0 to 10 carbon atoms, and examples thereof include an amino group, a methylamino group, a dimethylamino group, a diethylamino group, a dibenzylamino group, a diphenylamino group, and a ditolylamino group), an alkoxy group (preferably an alkoxy group having 1 to 30 carbon atoms, more preferably an alkoxy group having 1 to 20 carbon atoms, and particularly preferably an alkoxy group having 1 to 10 carbon atoms, and examples thereof include a methoxy group, an ethoxy group, a butoxy group, and a 2-ethylhexyloxy group), an aryloxy group (preferably an aryloxy group having 6 to 30 carbon atoms, more preferably an aryloxy group having 6 to 20 carbon atoms, and particularly preferably an aryloxy group having 6 to 12 carbon atoms, and examples thereof include a phenyloxy group, a 1-naphthyloxy group, and a 2-naphthyloxy group), a heterocyclic oxy group (preferably a heterocyclic oxy group having 2 to 30 carbon atoms, more preferably a heterocyclic oxy group having 2 to 20 carbon atoms, and particularly preferably a heterocyclic oxy group having 2 to 12 carbon atoms, and examples thereof include a pyridyloxy group, a pyrazyloxy group, a pyrimidyloxy group, and a quinolyloxy group), an acyl group (preferably an acyl group having 1 to 30 carbon atoms, more preferably an acyl group having 1 to 20 carbon atoms, and particularly preferably an acyl group having 1 to 12 carbon atoms, and examples thereof include an acetyl group, a benzoyl group, a formyl group, and a pivaloyl group), an alkoxycarbonyl group (preferably an alkoxycarbonyl group having 2 to 30 carbon atoms, more preferably an alkoxycarbonyl group having 2 to 20 carbon atoms, and particularly preferably an alkoxycarbonyl group having 2 to 12 carbon atoms, and examples thereof include a methoxycarbonyl group and an ethoxycarbonyl group), an aryloxycarbonyl group (preferably an aryloxycarbonyl group having 7 to 30 carbon atoms, more preferably an aryloxycarbonyl group having 7 to 20 carbon atoms, and particularly preferably an aryloxycarbonyl group having 7 to 12 carbon atoms, and examples thereof include a phenyloxycarbonyl group), an acyloxy group (preferably an acyloxy group having 2 to 30 carbon atoms, more preferably an acyloxy group having 2 to 20 carbon atoms, and particularly preferably an acyloxy group having 2 to 10 carbon atoms, and examples thereof include an acetoxy group and a benzoyloxy group), an acylamino group (preferably an acylamino group having 2 to 30 carbon atoms, more preferably an acylamino group having 2 to 20 carbon atoms, and particularly preferably an acylamino group having 2 to 10 carbon atoms, and examples thereof include an acetylamino group and a benzoylamino group), an alkoxycarbonylamino group (preferably an alkoxycarbonylamino group having 2 to 30 carbon atoms, more preferably an alkoxycarbonylamino group having 2 to 20 carbon atoms, and particularly preferably an alkoxycarbonylamino group having 2 to 12 carbon atoms, and examples thereof include a methoxycarbonylamino group), an aryloxycarbonylamino group (preferably an aryloxycarbonylamino group having 7 to 30 carbon atoms, more preferably an aryloxycarbonylamino group having 7 to 20 carbon atoms, and particularly preferably an aryloxycarbonylamino group having 7 to 12 carbon atoms, and examples thereof include a phenyloxycarbonylamino group), an alkyl or aryl sulfonylamino group (preferably having 1 to 30 carbon atoms, more preferably having 1 to 20 carbon atoms, and particularly preferably having 1 to 12 carbon atoms, and examples thereof include a methanesulfonylamino group, a benzenesulfonylamino group), a sulfamoyl group (including a sulfamoyl group and an alkyl or aryl sulfamoyl group, preferably a sulfamoyl group having 0 to 30 carbon atoms, more preferably a sulfamoyl group having 0 to 20 carbon atoms, and particularly preferably a sulfamoyl group having 0 to 12 carbon atoms, and examples thereof include a sulfamoyl group, a methylsulfamoyl group, a dimethylsulfamoyl group, and a phenylsulfamoyl group), a carbamoyl groups (including a carbamoyl group, an alkyl or aryl carbamoyl group, preferably a carbamoyl group having 1 to 30 carbon atoms, more preferably a carbamoyl group having 1 to 20 carbon atoms, and particularly preferably a carbamoyl group having 1 to 12 carbon atoms, and examples thereof include a carbamoyl group, a methylcarbamoyl group, a diethylcarbamoyl group, and a phenylcarbamoyl group), an alkylthio group (preferably an alkylthio group having 1 to 30 carbon atoms, more preferably an alkylthio group having 1 to 20 carbon atoms, and particularly preferably an alkylthio group having 1 to 12 carbon atoms, and examples thereof include a methylthio group and an ethylthio group), an arylthio group (preferably an arylthio group having 6 to 30 carbon atoms, more preferably an arylthio group having 6 to 20 carbon atoms, and particularly preferably an arylthio group having 6 to 12 carbon atoms, and examples thereof include a phenylthio group), an heterocyclic thio group (preferably an heterocyclic thio group having 2 to 30 carbon atoms, more preferably an heterocyclic thio group having 2 to 20 carbon atoms, and particularly preferably an heterocyclic thio group having 2 to 12 carbon atoms, and examples thereof include a pyridylthio group, a 2-benzimidazolylthio group, a 2-benzoxazolylthio group, and a 2-benzothiazolylthio group), an alkyl or aryl sulfonyl group (preferably an alkyl or aryl sulfonyl group having 1 to 30 carbon atoms, more preferably an alkyl or aryl sulfonyl group having 1 to 20 carbon atoms, and particularly preferably an alkyl or aryl sulfonyl group having 1 to 12 carbon atoms, and examples thereof include a mesyl group and a tosyl group), an alkyl or aryl sulfinyl group (preferably an alkyl or aryl sulfinyl group having 1 to 30 carbon atoms, more preferably an alkyl or aryl sulfinyl group having 1 to 20 carbon atoms, and particularly preferably an alkyl or aryl sulfinyl group having 1 to 12 carbon atoms, and examples thereof include a methanesulfinyl group and a benzenesulfinyl group), a ureido group (preferably a ureido group having 1 to 30 carbon atoms, more preferably a ureido group having 1 to 20 carbon atoms, and particularly preferably a ureido groups having 1 to 12 carbon atoms, and examples thereof include a ureido group, a methylureido group, and a phenylureido group), a phosphoric amide group (preferably a phosphoric amide group having 1 to 30 carbon atoms, more preferably a phosphoric amide group having 1 to 20 carbon atoms, and particularly preferably a phosphoric amide group having 1 to 12 carbon atoms, and examples thereof include a diethylphosphoric amide group and a phenylphosphoric amide group), a hydroxy group, a mercapto group, a halogen atom (for example, a fluorine atom, a chlorine atom, a bromine atom, and an iodine atom, and more preferably a fluorine atom), a cyano group, a sulfo group, a carboxyl group, an oxo group, a nitro group, a hydroxamic acid group, a sulfino group, a hydrazino group, an imino group, a heterocyclic group (preferably a heterocyclic group having 1 to 30 carbon atoms and more preferably a heterocyclic group having 1 to 12 carbon atoms, and as a heterocyclic atom configuring a ring structure, a nitrogen atom, an oxygen atom, or a sulfur atom is preferable, and specific examples thereof include an imidazolyl group, a pyridyl group, a quinolyl group, a furyl group, a thienyl group, a piperidyl group, a morpholino group, a benzoxazolyl group, a benzimidazolyl group, a benzothiazolyl group, a carbazolyl group, and an azepinyl group), a silyl group (preferably a silyl group having 3 to 40 carbon atoms, more preferably a silyl group having 3 to 30 carbon atoms, and particularly preferably a silyl group having 3 to 24 carbon atoms, and examples thereof include a trimethylsilyl group and a triphenylsilyl group), and a silyloxy group (preferably a silyloxy group having 3 to 40 carbon atoms, more preferably a silyloxy group having 3 to 30 carbon atoms, and particularly preferably a silyloxy group having 3 to 24 carbon atoms, and examples thereof include a trimethylsilyloxy group and a triphenylsilyloxy group).

These substituents may be further substituted with any one or more substituents selected from the above substituent group α.

Moreover, in the present invention, when there are a plurality of substituents in one structural portion, these substituents may be linked to each other to form a ring, or may be condensed with a part or all parts of the structural portion to form an aromatic ring or an unsaturated heterocycle.

<Polymerization Initiator>

The composition of the present invention is preferably polymerized and cured in the presence of a polymerization initiator, and accordingly, a polymerization initiator is preferably included in the composition.

Among polymerization initiators, in the present invention, a photopolymerization initiator capable of polymerizing by irradiation with active radiation is preferable.

Examples of the photopolymerization initiator include aromatic ketones, an acylphosphine compound, an aromatic onium salt compound, an organic peroxide, a thio compound, a hexaarylbiimidazole compound, a ketoxime ester compound, a borate compound, an azinium compound, a metallocene compound, an active ester compound, a compound having a carbon halogen bond, and an alkyl amine compound.

Preferable examples of the aromatic ketones, the acylphosphine oxide compound, and the thio compound include compounds having a benzophenone skeleton or a thioxanthone skeleton described in "RADIATION CURING IN POLYMER SCIENCE AND TECHNOLOGY", pp. 77-117 (1993). More preferable examples thereof include an α-thiobenzophenone compound described in JP1972-6416B (JP-S47-6416B), a benzoin ether compound described in JP1972-3981B (JP-S47-3981B), an α-substituted benzoin compound described in JP1972-22326B (JP-S47-22326B), a benzoin derivative described in JP1972-23664B (JP-S47-23664B), an aroylphosphonic acid ester described in JP1982-30704A (JP-S57-30704A), dialkoxybenzophenone described in JP1985-26483B (JP-S60-26483B), benzoin ethers described in JP1985-26403B (JP-S60-26403B) and JP1987-81345A (JP-S62-81345A), α-amino benzophenones described in JP1989-34242B (JP-H01-34242B), U.S. Pat. No. 4,318,791A, and EP0284561A1, p-di(dimethylaminobenzoyl)benzene described in JP1990-211452A (JP-H02-211452A), a thio substituted aromatic ketone described in JP1986-194062A (JP-S61-194062A), an acylphosphine sulfide described in JP1990-9597B (JP-H02-9597B), an acylphosphine described in JP1990-9596B (JP-H02-9596B), thioxanthones described in JP1988-61950B (JP-S63-61950B), and coumarins described in JP1984-42864B (JP-S59-42864B). In addition, the polymerization initiators described in JP2008-105379A and JP2009-114290A are also preferable. In addition, polymerization initiators described in pp. 65 to 148 of "Ultraviolet Curing System" written by Kato Kiyomi (published by Research Center Co., Ltd., 1989) can be exemplified.

In the present invention, a water-soluble polymerization initiator is preferable.

Here, "the polymerization initiator is water-soluble" means that 0.1% by mass or greater of the polymerization initiator dissolves with respect to distilled water at 25° C. The water-soluble photopolymerization initiator more preferably dissolves at 1% by mass or greater and particularly preferably at 3% by mass or greater with respect to distilled water at 25° C.

In the present invention, the content of the polymerization initiator is preferably 0.1% by mass to 10% by mass, more preferably 0.1% by mass to 5% by mass, and still more preferably 0.3% by mass to 2% by mass, with respect to 100 parts by mass of the total solid content mass in the composition.

<Polymerization Inhibitor>

In the present invention, a polymerization inhibitor is also preferably included in the composition.

As the polymerization inhibitor, known polymerization inhibitors can be used, and examples thereof include a phenol compound, a hydroquinone compound, an amine compound, and a mercapto compound.

Specific examples of the phenol compound include hindered phenol (a phenol having a t-butyl group at an ortho-position, and representative examples thereof include 2,6-di-t-butyl-4-methylphenol) and bisphenol. Specific examples of the hydroquinone compound include monomethyl ether hydroquinone. In addition, specific examples of the amine compound include N-nitroso-N-phenylhydroxylamine and N,N-diethylhydroxylamine.

Moreover, these polymerization inhibitors may be used alone or in combination of two or more types thereof.

The content of the polymerization inhibitor is preferably 0.01 parts by mass to 5 parts by mass, more preferably 0.01 parts by mass to 1 part by mass, and still more preferably 0.01 parts by mass to 0.5 parts by mass, with respect to 100 parts by mass of the total solid content mass in the composition.

<Solvent>

The composition of the present invention may include a solvent. The content of the solvent in the composition is preferably 5% by mass to 40% by mass, more preferably 10% by mass to 40% by mass, and still more preferably 20% by mass to 40% by mass, with respect to the total amount of composition.

By including a solvent, a curing (polymerization) reaction proceeds uniformly and smoothly. In addition, in a case where a porous support is impregnated with the composition, impregnation proceeds smoothly.

As the solvent, water, or a mixed solvent of water and a solvent having a solubility with respect to water of 5% by mass or greater are preferably used, and the solvent is preferably freely mixed with water. Thus, a solvent selected from water and an water-soluble solvent is preferable.

As the water-soluble solvent, in particular, an alcohol-based solvent, or an ether-based solvent, an amide-based solvent, a ketone-based solvent, a sulfoxide-based solvent, a sulfone-based solvent, a nitrile-based solvent, or an organic phosphorus-based solvent, which is an aprotic polar solvent, is preferable.

Examples of the alcohol-based solvent include methanol, ethanol, isopropanol, n-butanol, ethylene glycol, propylene glycol, diethylene glycol, and dipropylene glycol. These can be used alone or in combination of two or more types thereof.

In addition, preferable examples of the aprotic polar solvent include dimethyl sulfoxide, dimethyl imidazolidinone, sulfolane, N-methyl pyrrolidone, dimethyl formamide, acetonitrile, acetone, dioxane, tetramethyl urea, hexamethyl phosphoramide, hexamethyl phosphorotriamide, pyridine, propionitrile, butanone, cyclohexanone, tetrahydrofuran, tetrahydropyran, ethylene glycol diacetate, and γ-butyrolactone, and among these, dimethyl sulfoxide, N-methyl pyrrolidone, dimethyl formamide, dimethyl imidazolidinone, sulfolane, acetone, acetonitrile, or tetrahydrofuran. These can be used alone or in combination of two or more types thereof.

<Other Components>

The composition of the present invention may include a surfactant, a polymer dispersant, a viscosity improver, a surface tension adjuster, a preservative, an anti-crater agent, or the like, in addition to the above-described components.

<<Polymer Functional Cured Product>>

The polymer functional cured product includes a polymer having a structural unit represented by the following General Formula (I-1) or (I-2).

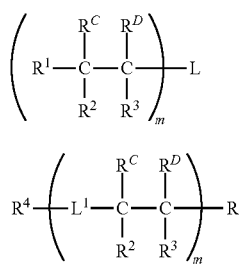

General Formula (I-1)

General Formula (I-2)

In General Formulas (I-1) and (I-2), m represents an integer of 2 or greater, and L represents an m-valent group or a single bond. Here, in a case where L is a single bond, m is 2. $L^1$ and $L^2$ each independently represent a single bond or a divalent linking group. $R^1$ to $R^5$ each independently represent a hydrogen atom or a substituent, and may be bonded to each other to form a ring, and may be bonded to L, $L^1$, or $L^2$ to form a ring. Either one of $R^C$ and $R^D$ represents a group represented by General Formula (a), and the other represents a group represented by the following General Formula (c). Here, m $-[C(R^3)(R^D)-C(R^1)(R^2)(R^C)]$'s may be the same as or different from each other, m $-[L^2-C(R^3)(R^D)-C(R^2)(R^C)-L^1]$-'s may be the same as or different from each other, and in m $-[C(R^3)(R^D)-C(R^1)(R^2)(R^C)]$'s or m $-[L^2-C(R^3)(R^D)-C(R^2)(R^C)-L^1]$-'s, $R^C$ or $R^D$ may be substituted with the group represented by the following General Formula (a).

$R^2$, $R^3$, and m in General Formulas (I-1) and (I-2) have the same meaning as $R^2$, $R^3$, and m in General Formulas (1-1) and (1-2), respectively, and the preferable ranges thereof are also the same. $R^1$ and L in General Formula (I-1) have the same meaning as $R^1$ and L in General Formula (1-1), respectively, and the preferable ranges thereof are also the same. $R^4$, $R^5$, $L^1$, and $L^2$ in General Formula (I-2) have the same meaning as $R^4$, $R^5$, $L^1$, and $L^2$ in General Formula (1-2), respectively, and the preferable ranges thereof are also the same.

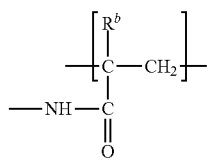

General Formula (c)

$R^b$ in General Formula (c) has the same meaning as $R^b$ in General Formula (b), and the preferable range thereof is also the same.

In the present invention, the structural unit represented by General Formula (I-1) is preferably a structural unit represented by the following General Formula (II).

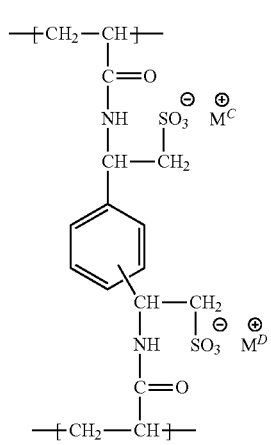

General Formula (II)

In General Formula (II), $M^C$ and $M^D$ have the same meaning as $M^A$ in General Formula (a), respectively, and the preferable ranges thereof are also the same.

<Support>

In a case where the polymer functional cured product of the present invention is used as, an ion-exchange membrane, in particular, a cation-exchange membrane, the polymer functional cured product of the present invention may have a support. Hereinafter, the ion-exchange membrane will be described in replacement of the polymer functional cured product.

To provide an ion-exchange membrane having good mechanical strength, a number of techniques can be used. For example, as a reinforcing material, a support can be used, and a porous support can be preferably used. By the polymerization and curing reaction after the composition is applied to the porous support and/or after the porous support is impregnated with the composition, a part of a membrane can be configured.

Examples of the porous support as a reinforcing material include synthetic woven fabric or synthetic non-woven fabric, a sponge-like film, and a film having fine through holes. The material for forming the porous support of the present invention can be a porous membrane based on, for example, polyolefin (polyethylene, polypropylene, or the like), polyacrylonitrile, polyvinyl chloride, polyester, polyamide, or copolymers thereof, or, for example, polysulfone, polyether sulfone, polyphenylene sulfone, polyphenylene sulfide, polyimide, polyethermide, polyamide, polyamideimide, polyacrylonitrile, polycarbonate, polyacrylate, cellulose acetate, polypropylene, poly(4-methyl-1-pentene), polyvinylidene fluoride, polytetrafluoroethylene, polyhexafluoropropylene, polychlorotrifluoroethylene, or copolymers thereof. Among these, in the present invention, polyolefin is preferable.

As the commercially available porous support and reinforcing material, products from Nippon Vilene Co., Ltd., Freudenberg Filtration Technologies (Novatexx material), or Sefar AG are commercially available.

Moreover, in the case of performing a photopolymerization and curing reaction, the porous support and the reinforcing material are required not to shield the wavelength range of the irradiation light, that is, are required to transmit irradiation light with wavelengths used in the polymerization and curing, but in the case of thermal polymerization and curing, there is no need to consider this point. In addition, the porous support and the reinforcing material are preferably a porous support and a reinforcing material into which the curable composition for forming an ion-exchange membrane is likely to penetrate.

The porous support and the reinforcing material preferably have hydrophilicity. To impart hydrophilicity to the support, a general method such as a corona treatment, an ozone treatment, a sulfuric acid treatment, or a silane coupling agent treatment can be used.

The thickness of the membrane of the present invention is preferably 30 μm to 150 μm, more preferably 50 μm to 130 μm, and particularly preferably 60 μm to 110 μm, in the case of having a support, including the support.

Here, as performed in the examples, the thickness of the membrane of the present invention is, specifically, a thickness after being stored for 12 hours in a 0.1 M NaCl solution.

<<Characteristics of Ion-Exchange Membrane>>

In a case where the polymer functional cured product of the present invention is used as an ion-exchange membrane, the polymer functional cured product preferably has the following characteristics.

Permselectivity (transport number): preferably 0.95 or greater, more preferably 0.97 or greater, still more preferably 0.99 or greater, and particularly preferably 1.00 or greater.

Product of electric resistance ($\Omega \cdot cm^2$) and water permeability ($mL/m^2/Pa/hr$) for a membrane: preferably $2.0 \times 10^{-4}$ or less, more preferably $1.7 \times 10^{-4}$ or less, still more preferably $1.6 \times 10^{-4}$ or less, and particularly preferably $1.5 \times 10^{-4}$ or less. Although the lower limit thereof is not particularly limited, the lower limit is practically 1.0 to $10^{-6}$.

<<Method for Manufacturing Polymer Functional Cured Product>>

The method for manufacturing the polymer functional cured product of the present invention will be described using a method for manufacturing an ion-exchange membrane which is most preferable for the use.

The ion-exchange membrane which is the polymer functional cured product of the present invention can be prepared by using a fixed support by a batch type method (a batch mode), and can also be prepared by using a support which moves by a continuous type method (a continuous mode). The support may be a roll shape in which continuous rewinding is performed. Moreover, in the case of a membrane is prepared by the continuous mode, a step of forming a membrane by mounting a support on a belt which continuously moves, by continuously applying a coating solution which is a curable composition for forming an ion-exchange membrane, and by polymerizing and curing can be continuously performed. Here, only one of a coating step and a film forming step may be continuously performed.

Moreover, separately from the support, while a porous support is impregnated with the curable composition for forming an ion-exchange membrane and the polymerization and curing reaction is completed, a temporary support (after the polymerization and curing reaction ends, the membrane is peeled off from the temporary support) may be used.

In such a temporary support, it is not necessary to consider substance permeation, and for example, the temporary support may be any one as long as it includes a polyethylene terephthalate (PET) film or a metal plate such as an aluminum plate and can be fixed for formation of a membrane.

In addition, a porous support is impregnated with the curable composition for forming an ion-exchange membrane, and can also be polymerized and cured without using a support other than the porous support.

The curable composition for forming an ion-exchange membrane can be applied to the porous support or the porous support can be impregnated with the composition by various method, for example, curtain coating, extrusion coating, air knife coating, slide coating, nip roll coating, forward roll coating, reverse roll coating, dip coating, kiss coating, rod bar coating, and spray coating. Coating of a plurality of layers can be performed simultaneously or sequentially. In simultaneous multilayer coating, curtain coating, slide coating, slot die coating, or extrusion coating is preferable.

In manufacture of an ion-exchange membrane in the continuous mode, a membrane is manufactured by continuously applying the curable composition for forming an ion-exchange membrane to a support which moves, and more preferably, is manufactured by a manufacture unit including a curable composition coating portion, an irradiation source for polymerizing and curing the curable composition, a membrane collecting portion for collecting the formed membrane, and means for moving the support from the curable composition coating portion to the irradiation source and the membrane collecting portion.

In the present manufacture example, an ion-exchange membrane is manufactured through a step (i) of applying the curable composition forming the ion-exchange membrane which is the polymer functional cured product of the present invention to a support (preferably, a porous support) and/or impregnating the support with the composition, a step (ii) of polymerizing and curing the curable composition by irradiation with active radiation or heating, and a step (iii) of taking out the formed membrane from the support, if desired.

Moreover, in the step (ii), heating may be performed in combination with irradiation with active radiation. In the step (i), the support is preferably impregnated with the curable composition.

[Irradiation with Active Radiation]

In the manufacture unit, the curable composition coating portion is provided at the upstream position with respect to a irradiation source, and the irradiation source is placed at the upstream position with respect to the membrane collecting portion.

To have sufficient fluidity when applying using a high speed coating machine, the viscosity of the curable composition for forming an ion-exchange membrane at 35° C. is preferably less than 4000 mPa·s, more preferably 1 mPa·s to 1000 mPa·s, and most preferably 1 mPa·s to 500 mPa·s. In the case of slide bead coating, the viscosity at 35° C. is preferably 1 mPa·s to 100 mPa·s.

In a high speed coating machine, the coating solution which is the curable composition for forming an ion-exchange membrane can be applied to a support which moves, at a speed greater than 15 m/min, and can also be applied at a speed greater than 400 m/min.

In particular, in a case where a support is used to increase the mechanical strength, before the curable composition of the present invention is applied to the surface of the support, the support may be subjected to a corona discharge treatment, a glow discharge treatment, a flame treatment, or an ultraviolet rays irradiation treatment, for example, to improve the wettability and the adhesion of the support.

The polymerization and curing of the composition of the curable composition for forming an ion-exchange membrane is initiated preferably within 60 seconds, more preferably within 15 seconds, particularly preferably within 5 seconds, and most preferably within 3 seconds after the curable composition is applied to the support or the support is impregnated with the composition.

Irradiation with active radiation for polymerization and curing is preferably performed for less than 10 seconds, more preferably for less than 5 seconds, particularly preferably for less than 3 seconds, and most preferably for less than 2 seconds. In a continuous method, irradiation is continuously performed, and in consideration of the speed at which the curable composition is moved through the irradiation beam, the polymerization and curing reaction time is determined.

In a case where ultraviolet rays (UV light) having a high intensity are used in the polymerization and curing reaction, a significant amount of heat is generated, and thus, to prevent overheating, it is preferable to cool the lamp of the light source and/or the support/membrane with a cooling air. In the case of being irradiated with a significant dose of infrared rays (IR light) together with a UV beam, irradiation with UV light is performed using an IR reflecting quartz plate as a filter.

As the active radiation, ultraviolet rays are preferable. The irradiation wavelength is preferably compatible with the absorption wavelength of any polymerization initiator included in the composition of the curable composition for forming an ion-exchange membrane and the curable composition, and for example, is UV-A (400 nm to 320 nm), UV-B (320 nm to 280 nm), and UV-C (280 nm to 200 nm).

Examples of the ultraviolet light source include a mercury arc lamp, a carbon arc lamp, a low pressure mercury lamp, a medium pressure mercury lamp, a high pressure mercury lamp, a swirling flow plasma arc lamp, a metal halide lamp, a xenon lamp, a tungsten lamp, a halogen lamp, laser, and an ultraviolet ray emitting diode. A medium pressure or high pressure mercury vapor type ultraviolet ray emitting lamp is particularly preferable. Additionally, to modify the emission spectrum of a lamp, an additive such as metal halide may be present. A lamp having an emission maximum at a wavelength of 200 nm to 450 nm is particularly suitable.

The energy output of the radiation source is preferably 20 W/cm to 1000 W/cm and more preferably 40 W/cm to 500 W/cm, and if a desired exposure dose can be achieved, but the energy output may be higher or lower than the desired exposure dose. By the exposure intensity, polymerization and curing of the film is adjusted. The exposure dose is measured by using a High Energy UV Radiometer (UV Power Puck™ manufactured by EIT-Instrument Markets) in a UV-A range shown in the device, and the exposure dose is preferably at least 40 mJ/cm$^2$ or greater, more preferably 100 mJ/cm$^2$ to 2,000 mJ/cm$^2$, and most preferably 150 mJ/cm$^2$ to 1,500 mJ/cm$^2$. The exposure time can be freely selected, and is preferably short, and most preferably less than 2 seconds.

To reach the desired dose in a fast coating speed, a plurality of light sources may be used. The exposure intensities of these light sources may be the same as or different from each other.

[Polymerization and Curing by Heating]

Even in a case where the ion-exchange membrane which is the polymer functional cured product of the present invention is manufactured by thermal polymerization and curing, the membrane having almost the same properties is obtained. In the thermal polymerization and curing, the heating temperature is preferably 40° C. to 200° C., more preferably 60° C. to 180° C., and particularly preferably 70° C. to 150° C. The heating time is preferably 5 minutes to 12 hours, more preferably 10 minutes to 10 hours, and particularly preferably 10 minutes to 8 hours.

<<Water-Soluble Acrylamide Compound>>

The water-soluble acrylamide monomer is a water-soluble acrylamide compound, and "monomer" is an application.

Accordingly, the water-soluble acrylamide compound of the present invention is preferably the same compound as the above-described water-soluble acrylamide monomer.

<<Preparation Method for Water-Soluble Acrylamide Compound>>

The water-soluble acrylamide compound or monomer represented by General Formula (1-1) or (1-2) of the present invention can be manufactured in one step by reacting an olefin compound represented by the following General Formula (3-1) or (3-2) and acrylonitrile with fuming sulfuric acid.

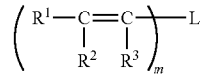

General Formula (3-1)

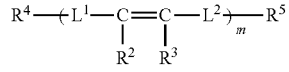

General Formula (3-2)

In General Formulas (3-1) and (3-2), m, L, L$^1$, L$^2$, and R$^1$ to R$^5$ have the same meaning as m, L, L$^1$, L$^2$, and R$^1$ to R$^5$ in General Formulas (1-1) and (1-2), respectively, and the preferable ranges thereof are also the same.

Among these, the olefin compound represented by General Formula (3-1) is preferably divinylbenzene.

Specific examples of the olefin compound represented by General Formula (3-1) or (3-2) are shown below, but the present invention is not limited thereto.

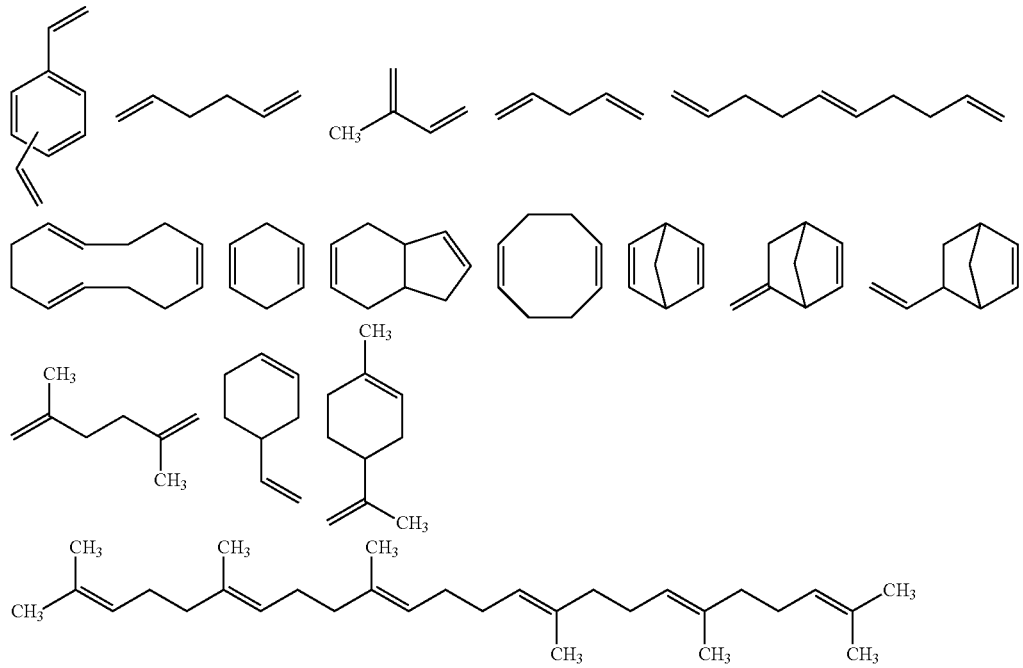

The fuming sulfuric acid is preferably fuming sulfuric acid having a concentration of 5% to 50%, and more preferably fuming sulfuric acid having a concentration of 15% to 35%.

Acrylonitrile is preferably 1 equivalent to 50 equivalents, more preferably 2 equivalents to 40 equivalents, and still more preferably 5 equivalents to 30 equivalents, with respect to 1 equivalent of ethylene in the olefin compound represented by General Formula (3-1) or (3-2).

$SO_3$ in fuming sulfuric acid is preferably 1 equivalent to 10 equivalents, more preferably 1 equivalent to 7 equivalents, and still more preferably 1 equivalent to 5 equivalents, with respect to 1 equivalent of ethylene in the olefin compound represented by General Formula (3-1) or (3-2).

Moreover, in the reaction, acrylonitrile may be used as a reaction solvent, or other solvents may be used.

Examples of other solvents include 1,2-dichloroethane, 1,4-dioxane, dichloromethane, chloroform, and carbon tetrachloride.

However, typically, the olefin compound represented by General Formula (3-1) or (3-2) is a liquid, and thus, in the reaction, a solvent is not used.

The reaction temperature is preferably −10° C. to 60° C., more preferably 0° C. to 50° C., and still more preferably 10° C. to 40° C.

By the reaction, a sulfonic acid (—$SO_3H$) compound is obtained, then, by neutralizing this sulfonic acid compound with an inorganic or organic base, an inorganic or organic salt of sulfonic acid is obtained, this can be a salt of $M^A$, $M^C$, or $M^D$.

<<Applications of Polymer Functional Cured Product>>

As described above, the polymer functional cured product of the present invention is useful as an ion-exchange membrane, particularly, an cation-exchange membrane, and a proton conductive membrane, and can be used in electrodeionization, continuous electrodeionization, electrodialysis, reverse electrodialysis, a reverse osmosis membrane, a forward osmosis membrane, a polymer electrolyte, a water-absorbing resin, or a gas separation membrane. In addition, the polymer functional cured product of the present invention can be used in not only general applications but also medical applications, and in recent years, used in a solid polymer electrolyte type fuel cell.

EXAMPLES

Hereinafter, the present invention will be described in more detail with reference to examples, but the present invention is not limited to the examples. Moreover, "parts" and "%" are based on mass unless specified otherwise.

<Synthesis Example of Water-Soluble Acrylamide Monomer (Compound) of Present Invention>

(Synthesis of Compound (M-1))

A compound (M-1) was synthesized by the following synthesis scheme.

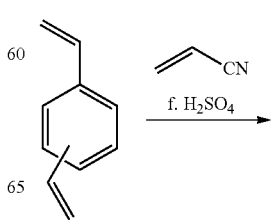

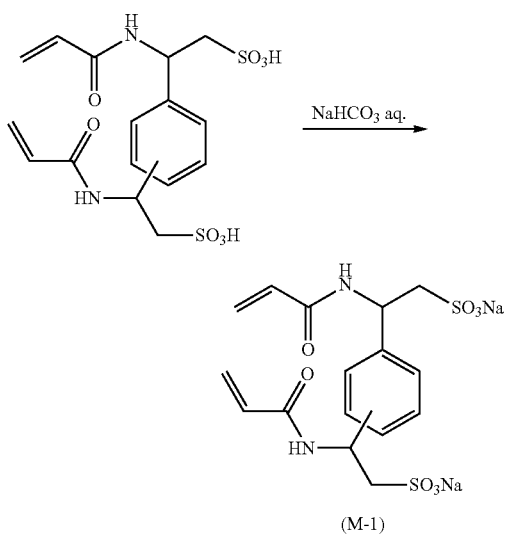

(M-1)

115.2 mL (2.34 mol) of 25% fuming sulfuric acid (manufactured by Wako Pure Chemical Industries, Ltd.) was added a mixed solution of 42.04 mL (0.30 mol) of divinylbenzene (manufactured by Tokyo Chemical Industry Co., Ltd.) and 884.3 mL (13.5 mol) of acrylonitrile (manufactured by Tokyo Chemical Industry Co., Ltd.) at −10° C. to −5° C., and the resultant product was stirred at room temperature for 3 hours. Thereafter, 300 mL of water and 394 g of sodium hydrogen carbonate were added thereto at 0° C., then, 2.4 L of methanol was added thereto, and the precipitate was separated by filtration. After the filtrate was concentrated, 3 L of acetonitrile was added thereto, and the resultant product was filtered, whereby 37.5 g of a compound (M-1) was obtained as pale yellow crystals.

$^1$H-NMR (DMSO-d6) δ:2.73 (dd, 2H, J=3.2 Hz, 13.8 Hz, CH$_2$SO$_3$), 2.95 (dd, 2H, J=9.8 Hz, 13.8 Hz, CH$_2$SO$_3$), 5.14 (ddd, 2H, J=3.2 Hz, 9.8 Hz, 7.0 Hz, ArCH), 5.55 (dd, 2H, J=2.6 Hz, 10.1 Hz, —CH=CH$_2$), 6.03 (dd, 2H, J=2.6 Hz, 17.1 Hz, —CH=CH$_2$), 6.25 (dd, 2H, J=10.1 Hz, 17.1 Hz, —CH=CH$_2$), 7.00-7.24 (m, 4H, Ar), 8.51 (d, 2H, J=7.0 Hz, NH)

(Synthesis of Compound (M-2))

A compound (M-2) was synthesized by the following synthesis scheme.

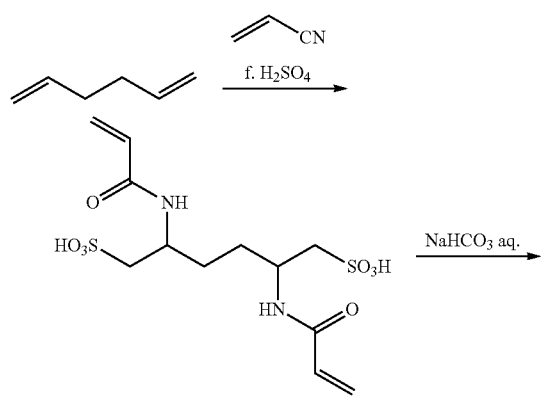

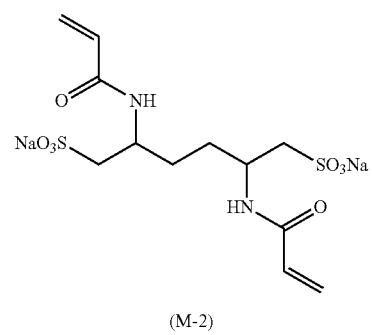

(M-2)

A compound (M-2) was obtained in the same manner as in the compound (M-1) using an equimolar amount of 1,5-hexadiene (manufactured by Tokyo Chemical Industry Co., Ltd.) instead of divinylbenzene.

(Synthesis of Compound (M-3))

A compound (M-3) was synthesized by the following synthesis scheme.

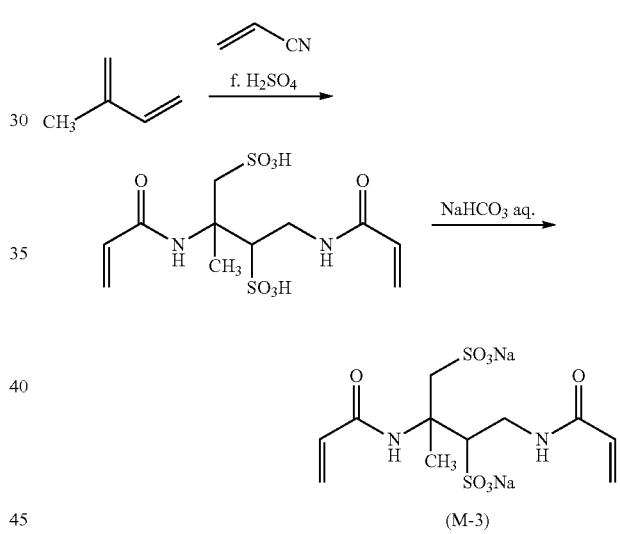

(M-3)

A compound (M-3) was obtained in the same manner as in the compound (M-1) using an equimolar amount of isoprene (manufactured by Tokyo Chemical Industry Co., Ltd.) instead of divinylbenzene.

(Synthesis of Compound (M-4))

A compound (M-4) was synthesized by the following synthesis scheme.

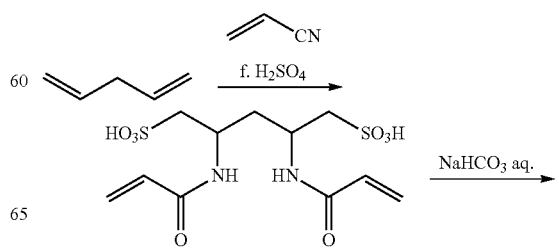

-continued

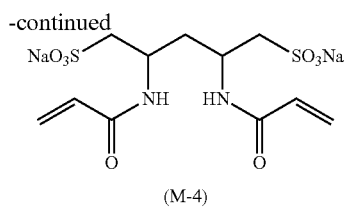

(M-4)

A compound (M-4) was obtained in the same manner as in the compound (M-1) using an equimolar amount of 1,4-pentadiene (manufactured by Sigma-Aldrich Co.) instead of divinylbenzene.

(Synthesis of Compound (M-5))

A compound (M-5) was synthesized by the following synthesis scheme.

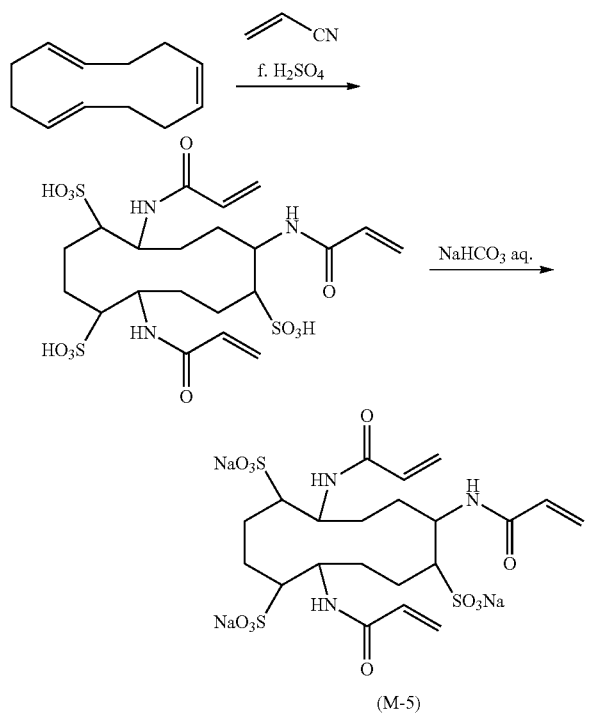

(M-5)

A compound (M-5) was obtained in the same manner as in the compound (M-1) using an equimolar amount of 1,5,9-cyclododecatriene (manufactured by Tokyo Chemical Industry Co., Ltd.) instead of divinylbenzene.

Example 1

(Production of Ion-Exchange Membrane)

A coating solution formed of a composition having a composition (unit: g) shown in the following Table 1 was manually applied to an aluminum plate at a speed of about 5 m/min using a wire bar (a stainless steel bar on which a wire of 150 μm had been wound at about 1 lap/3 cm (length direction)), and then, non-woven fabric (manufactured by Freudenberg Group, product name: FO-2226-14) was impregnated with the coating solution. The excessive coating solution was removed by using a rod on which a wire had not been wound. Temperature of the coating liquid at the time of application was about 50° C. The coating solution-impregnated support obtained in the above manner was exposed for 0.47 seconds using a UV exposure machine (manufactured by Fusion UV Systems, Inc., Model Light Hammer LH6, D-bulb, speed of 15 m/min, 100% strength) to cause a polymerization and curing reaction for a polymerization curing time of 0.8 seconds, whereby a cation-exchange membrane was prepared. The obtained membrane was removed from the aluminum plate, and stored for at least 12 hours in a 0.1 M NaCl aqueous solution, whereby an ion-exchange membrane was produced.

Examples 2 to 10 and Comparative Examples 1 to 6

Ion-exchange membranes of Examples 2 to 10 and Comparative Examples 1 to 6 were respectively produced in the same manner as in Example 1 except that the composition in the production of the ion-exchange membrane of Example 1 was changed to the compositions described in the following Table 1.

Evaluation of the following items was performed on the ion-exchange membranes produced in Examples 1 to 10 and Comparative Examples 1 to 6.

[Permselectivity (Transport Number)]

The membrane potential (V) was measured by a static membrane potential measurement, and from this, the permselectivity was calculated. Two cells (electrolytic cells) were separated by a membrane which was a measuring object. Before measurement, a membrane was equilibrated in a 0.05 M NaCl aqueous solution for about 16 hours. Thereafter, NaCl aqueous solutions having different concentrations were poured into electrolytic cells on both sides facing a membrane which was a measuring object, respectively.

That is, 100 mL of a 0.05 M NaCl aqueous solution was poured into one cell. In addition, 100 mL of 0.5 M NaCl aqueous solution was poured into the other cell.

After the temperature of the NaCl aqueous solution in the cell was stably maintained at 25° C. in a constant temperature water bath, both electrolytic cells and a Ag/AgCl reference electrode (manufactured by Metrohm AG in Swiss) were connected through a salt bridge, then, the membrane potential (V) was measured while passing both solutions toward the membrane surfaces, and the permselectivity t was calculated by the following Equation (a). Moreover, the effective area of the membrane was 1 cm².

$$t=(a+b)/2b \qquad \text{Equation (a)}$$

The respective reference signs in Equation (a) mean the following.

a: membrane potential (V)

b: $0.5915 \log(f_1 c_1/f_2 c_2)$ (V)

$f_1, f_2$: activity coefficient of NaCl in both cells $c_1, c_2$: concentration (M) of NaCl in both cells

[Electric Resistance (Ω/cm²) of Membrane]

Both surfaces of the membrane immersed in a 0.5 M NaCl aqueous solution for 2 hours were wiped with a dry filter paper, and the membrane was put into two-chamber type cell (effective membrane area of 1 cm², an Ag/AgCl reference electrode (manufactured by Metrohm AG) as the electrode). Both chambers were filled with 100 mL of a NaCl aqueous solution having the same concentration and allowed to stand to until reaching equilibrium in a constant temperature water bath at 25° C., and after the liquid temperature in the cell became precisely 25° C., the electrical resistance $r_1$ was measured using an AC bridge (frequency of 1,000 Hz). The measurement NaCl aqueous solution concentration was 0.5 M, 0.7 M, 1.5 M, 3.5 M, and 4.5 M, and measurement was performed in this order from the low concentration solution.

Next, the membrane was removed, then, the electric resistance $r_2$ between two electrodes as only the 0.5 M NaCl aqueous solution was measured, and the electric resistance r of the membrane was determined from $r_1$-$r_2$.

In the following Table 1, "electric resistance of a membrane" is simply referred to as "membrane resistance".

[Water Permeability (mL/m²/Pa/hr)]

The water permeability for the membrane was measured by using a device having a flow path 10 shown in FIG. 1. In FIG. 1, a reference sign 1 represents a membrane, and reference signs 3 and 4 represent a flow path of a feed solution (pure water) and a flow path of a draw solution (3 M NaCl aqueous solution), respectively. In addition, arrows of a reference sign 2 show flow of water separated from the feed solution.

400 mL of the feed solution and 400 mL of the draw solution are brought into contact through the membrane (membrane contact area of 18 cm²), and each solution was passed at a flow rate of 0.11 cm/sec in the direction of the arrow of a reference sign 5 using a peristaltic pump. The speed at which water in the feed solution permeates into the draw solution through the membrane was analyzed by measuring the mass of the feed solution and the draw solution in real time, and the water permeability was determined.

Moreover, in Table 1, the water permeability is shown as a value obtained by multiplying by $10^5$. That is, 8.8 in Example 1 is 8.8×$10^{-5}$ (mL/m²/Pa/hr).

Here, evaluation is performed also as the value of the product of the electrical resistance of the membrane and the water permeability, and it is good that the electrical resistance of the membrane is low and the water permeability is also low, and as the result, it is good that the value of the product of the electrical resistance of the membrane and the water permeability is low.

In addition, the value of "the product of the electrical resistance of the membrane and the water permeability" is also simply referred to as "(membrane resistance)×(water permeability)", and the value is shown as a value obtained by multiplying by $10^4$. That is, 1.5 in Example 1 is 15×$10^{-4}$ (Ω·cm²·mL/m²/Pa/hr).

[Pinhole Test]

The membrane for measurement was coated with Pt at a thickness of 1.5 nm, and using a scanning electron microscope (SEM), the number of pin holes in 1 mm² thereof was examined.

(Measurement Conditions)

Measurement apparatus model: Hitachi S-3200H SEM, manufactured by Hitachi High-Technologies Corporation Accelerating voltage: 2 kV Working distance: 4 mm Aperture: 4

Magnification: ×1,000 times

Inclination of viewing field: 3°

Evaluation of pinholes was performed from SEM image from the following viewpoint.

(Evaluation Criteria)

A: pass, pinholes were not observed.

B: defect, 1 or 2 pinholes were observed.

C: defect, 3 or more pinholes were observed.

The obtained results are collectively shown in Table 1 below.

Moreover, abbreviations of the compounds described in Table 1 are the following compounds.

Here, a compound having one polymerizable group was classified as a monofunctional monomer, and a compound having two or more polymerizable groups was classified as a crosslinking agent, and these are shown in Table 1.

Monofunctional Monomer (Water-Soluble Acrylamide Monomer Represented by General Formula (M))

AMPS: 2-acrylamide-2-methylpropanesulfonic acid (manufactured by Tokyo Chemical Industry Co., Ltd.)

Crosslinking Agent

MBA: methylenebisacrylamide (manufactured by Tokyo Chemical Industry Co., Ltd.)

BAP: 1,4-bis(acryloyl)piperazine (manufactured by Sigma-Aldrich Co.)

EGDM: ethylene glycol dimethacrylate (manufactured by Tokyo Chemical Industry Co., Ltd.)

TEGDM: triethylene glycol dimethacrylate (manufactured by Tokyo Chemical Industry Co., Ltd.)

Polymerization Inhibitor

MEHQ: monomethyl ether hydroquinone (manufactured by Tokyo Chemical Industry Co., Ltd.)

Polymerization Initiator

Darocur 1173: product name, manufactured by Ciba Specialty Chemicals Inc

Irgacure 2959: product name, manufactured by BASF Japan Co., Ltd.

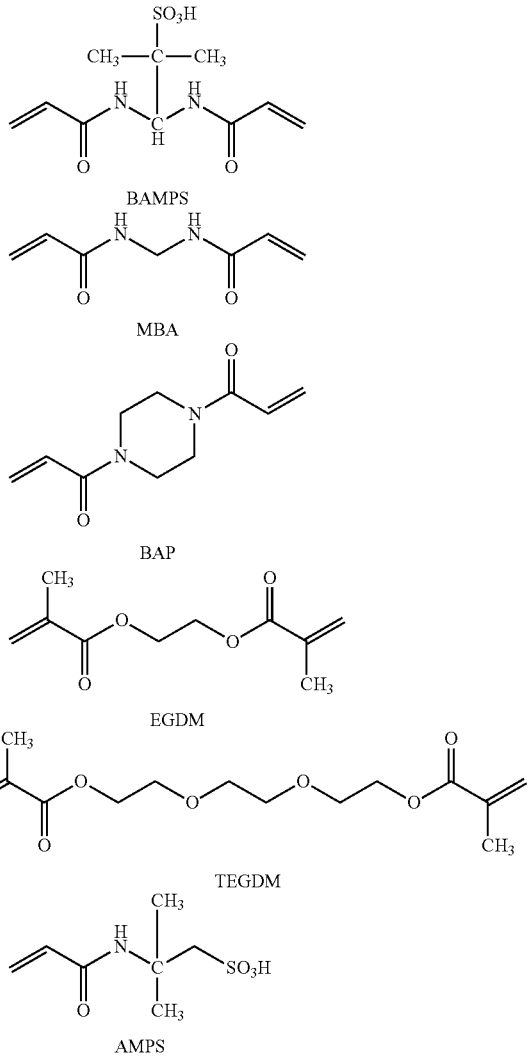

Here, BAMPS is a compound described in U.S. Pat. No. 4,034,001A.

TABLE 1

| Items | Types | | Example 1 | Example 2 | Example 3 | Example 4 | Example 5 | Example 6 | Example 7 | Example 8 | Example 9 | Example 10 |
|---|---|---|---|---|---|---|---|---|---|---|---|---|
| Monofunctional monomer | AMPS | | | | | | | 10.0 | 20.0 | 30.0 | 40.0 | 10.0 |
| Crosslinking agent | Compound represented by General Formula (1-1) or (1-2) | Compound (M-1) | 61.8 | | | | | 51.8 | | | | |
| | | Compound (M-2) | | 61.8 | | | | | 41.8 | | | |
| | | Compound (M-3) | | | 61.8 | | | | | 31.8 | | |
| | | Compound (M-4) | | | | 61.8 | | | | | 21.8 | |
| | | Compound (M-5) | | | | | 61.8 | | | | | 51.8 |
| | BAMPS | | | | | | | | | | | |
| | MBA | | | | | | | | | | | |
| | BAP | | | | | | | | | | | |
| | EGDM | | | | | | | | | | | |
| | TEGDM | | | | | | | | | | | |
| Polymerization inhibitor | MEHQ | | 0.1 | 0.1 | 0.1 | 0.1 | 0.1 | 0.1 | 0.1 | 0.1 | 0.1 | 0.1 |
| Polymerization initiator | Darocur 1173 | | 0.5 | 0.5 | 0.5 | 0.5 | 0.5 | 0.5 | 0.5 | 0.5 | 0.5 | 0.5 |
| | Irgacure 2959 | | 0.5 | 0.5 | 0.5 | 0.5 | 0.5 | 0.5 | 0.5 | 0.5 | 0.5 | 0.5 |
| Solvent | Pure water | | 37.1 | 37.1 | 37.1 | 37.1 | 37.1 | 37.1 | 37.1 | 37.1 | 37.1 | 37.1 |
| | Total mass | | 100 | 100 | 100 | 100 | 100 | 100 | 100 | 100 | 100 | 100 |
| Mass ratio [% by mass] | Polymerization component[1] [% by mass] | | 61.8 | 61.8 | 61.8 | 61.8 | 61.8 | 61.8 | 61.8 | 61.8 | 61.8 | 61.8 |
| | Solvent[2] [% by mass] | | 37.1 | 37.1 | 37.1 | 37.1 | 37.1 | 37.1 | 37.1 | 37.1 | 37.1 | 37.1 |
| | Monomer[3] [% by mass] | | 0.0 | 0.0 | 0.0 | 0.0 | 0.0 | 16.2 | 32.4 | 48.5 | 64.7 | 16.2 |
| | Crosslinking agent[4] [% by mass] | | 100.0 | 100.0 | 100.0 | 100.0 | 100.0 | 83.8 | 67.6 | 51.5 | 35.3 | 83.8 |
| | Polymerization initiator[5] [% by mass] | | 1.6 | 1.6 | 1.6 | 1.6 | 1.6 | 1.6 | 1.6 | 1.6 | 1.6 | 1.6 |
| Evaluation items | Permselectivity | | 1.00 | 1.00 | 1.00 | 1.00 | 1.00 | 1.00 | 1.00 | 0.99 | 0.99 | 1.00 |
| | Membrane resistance ($\Omega \cdot cm^2$) | | 1.7 | 1.6 | 1.5 | 1.5 | 2.1 | 1.4 | 1.3 | 1.2 | 1.1 | 1.7 |
| | Water permeability ($10^{-5}$ mL/m$^2$/Pa/hr) | | 8.8 | 9.2 | 9.9 | 9.8 | 7.4 | 11.2 | 13.4 | 14.5 | 15.6 | 10.2 |
| | (membrane resistance) × (water permeability) | | 1.5 | 1.5 | 1.5 | 1.5 | 1.6 | 1.6 | 1.7 | 1.7 | 1.7 | 1.7 |
| | Pinhole test | | A | A | A | A | A | A | A | A | A | A |

| Items | Types | | Comparative Example 1 | Comparative Example 2 | Comparative Example 3 | Comparative Example 4 | Comparative Example 5 | Comparative Example 6 |
|---|---|---|---|---|---|---|---|---|
| Monofunctional monomer | AMPS | | | 30.0 | 30.0 | 30.0 | 30.0 | 30.0 |
| Crosslinking agent | Compound represented by General Formula (1-1) or (1-2) | Compound (M-1) | | | | | | |
| | | Compound (M-2) | | | | | | |
| | | Compound (M-3) | | | | | | |
| | | Compound (M-4) | | | | | | |
| | | Compound (M-5) | | | | | | |
| | BAMPS | | 61.8 | 31.8 | | | | |
| | MBA | | | | 31.8 | | | |
| | BAP | | | | | 31.8 | | |
| | EGDM | | | | | | 31.8 | |
| | TEGDM | | | | | | | 31.8 |
| Polymerization inhibitor | MEHQ | | 0.1 | 0.1 | 0.1 | 0.1 | 0.1 | 0.1 |
| Polymerization initiator | Darocur 1173 | | 0.5 | 0.5 | 0.5 | 0.5 | 0.5 | 0.5 |
| | Irgacure 2959 | | 0.5 | 0.5 | 0.5 | 0.5 | 0.5 | 0.5 |
| Solvent | Pure water | | 37.1 | 37.1 | 37.1 | 37.1 | 37.1 | 37.1 |
| | Total mass | | 100 | 100 | 100 | 100 | 100 | 100 |
| Mass ratio [% by mass] | Polymerization component[1] [% by mass] | | 61.8 | 61.8 | 61.8 | 61.8 | 61.8 | 61.8 |
| | Solvent[2] [% by mass] | | 37.1 | 37.1 | 37.1 | 37.1 | 37.1 | 37.1 |
| | Monomer[3] [% by mass] | | 0.0 | 48.5 | 48.5 | 48.5 | 48.5 | 48.5 |
| | Crosslinking agent[4] [% by mass] | | 100.0 | 51.5 | 51.5 | 51.5 | 51.5 | 51.5 |
| | Polymerization initiator[5] [% by mass] | | 1.6 | 1.6 | 1.6 | 1.6 | 1.6 | 1.6 |

TABLE 1-continued

| Evaluation items | | | | | | | |
|---|---|---|---|---|---|---|---|
| | Permselectivity | 0.98 | 0.98 | 0.98 | Unmeasurable | Unmeasurable | Unmeasurable |
| | Membrane resistance ($\Omega \cdot cm^2$) | 4.3 | 1.7 | 1.9 | Unmeasurable | Unmeasurable | Unmeasurable |
| | Water permeability ($10^{-5}$ mL/m²/Pa/hr) | 5.2 | 12.5 | 11.3 | Unmeasurable | Unmeasurable | Unmeasurable |
| | (membrane resistance) × (water permeability) | 2.2 | 2.1 | 2.2 | Unmeasurable | Unmeasurable | Unmeasurable |
| | Pinhole test | B | B | B | C | C | C |

[1] Total mass ratio of a monomer and a crosslinking agent to the total mass
[2] Mass ratio of a solvent to the total mass
[3] Mass ratio of a monomer to the total of a monomer and a crosslinking agent
[4] Mass ratio of a crosslinking agent to the total of a monomer and a crosslinking agent
[5] Mass ratio of a polymerization initiator to the polymerization components (total of a monomer and a crosslinking agent)

As clearly seen from Table 1, it was found that since all the ion-exchange membranes of Examples 1 to 10 which satisfy the requirements of the present invention had a high value in permselectivity and a low value in the product of the electrical resistance of the membrane and the water permeability, the ion-exchange membranes are high performance ion-exchange membranes. In contrast, it was found that since the ion-exchange membrane of Comparative Example 1 which does not satisfy the requirements of the present invention had a great electric resistance of the membrane, the ion-exchange membrane is not suitable for electrodialysis or the like. In the ion-exchange membranes of Comparative Examples 2 and 3, the electric resistance of the membrane was not higher than that of the membrane of Comparative Example 1, and the product of the electrical resistance of the membrane and the water permeability was great. Membrane performance of the ion-exchange membranes of Comparative Examples 4 to 6 could not be evaluated since the ion-exchange membranes had many defects. Therefore, it can also be said that the ion-exchange membrane which satisfies the requirements of the present invention has sufficient advantages from the viewpoint of the basic characteristics of the ion-exchange membrane.

Although the present invention has been described with the embodiments thereof, unless otherwise particularly described, the present invention is not intended to be limited in any details of description of the present invention, and it is considered that the present invention must be broadly interpreted without departing from the spirit and the scope of the present invention shown in the appended claims.

EXPLANATION OF REFERENCES

1: membrane
2: arrow showing that water in feed solution permeates into a draw solution through a membrane
3: flow path of feed solution
4: flow path of draw solution
5: running direction of liquid
10: flow path of device for measuring coefficient of water permeability

What is claimed is:
1. A curable composition, comprising:
a water-soluble multi-acrylamide-containing monomer represented by the following General Formula (1-1) or (1-2),

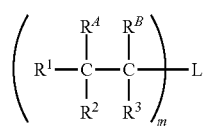

General Formula (1-1)

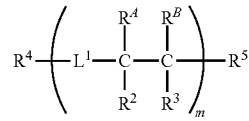

General Formula (1-2)

in General Formulas (1-1) and (1-2), m represents an integer of 2 or greater, and L represents an m-valent group or a single bond; here, in a case where L is a single bond, m is 2; $L^1$ and $L^2$ each independently represent a single bond or a divalent linking group; $R^1$ to $R^5$ each independently represent a hydrogen atom or a substituent, and may be bonded to each other to form a ring, and may be bonded to L, $L^1$, or $L^2$ to form a ring; at least one but not all of $R^A$ and $R^B$ represents a group represented by the following General Formula (a), and the other represents a group represented by the following General Formula (b); and here, m —[C($R^3$)($R^B$)—C($R^1$)($R^2$)($R^A$)]'s may be the same as or different from each other, m -[$L^2$-C($R^3$)($R^B$)—C($R^2$)($R^4$)-$L^1$]-'s may be the same as or different from each other, and in m—[C($R^3$)($R^B$)—C($R^1$)($R^2$)($R^A$)]'s or m—[$L^2$-C($R^3$)($R^B$)—C($R^2$)($R^A$)-$L^1$]-'s, $R^A$ or $R^B$ may be substituted with the group represented by the following General Formula (a); and

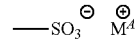

General Formula (a)

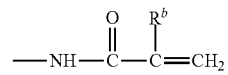

General Formula (b)

in General Formula (a), $M^A$ represents a hydrogen ion, an inorganic ion, or an organic ion; here, each of the inorganic ion and the organic ion may be a di- or higher valent ion; and in General Formula (b), $R^b$ represents a hydrogen atom or an alkyl group.

2. The curable composition according to claim 1, wherein m is 2, and L is a single bond, an alkylene group, or an arylene group.

3. The curable composition according to claim 2, wherein the water-soluble multi-acrylamide-containing monomer represented by General Formula (1-1) is represented by the following General Formula (2), and

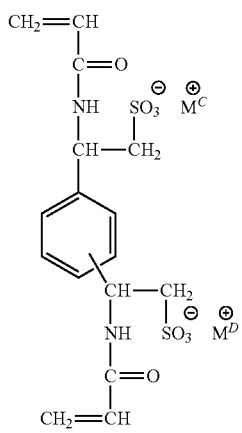

General Formula (2)

in General Formula (2), $M^C$ and $M^D$ each independently represent a hydrogen ion, an inorganic ion, or an organic ion; and here, each of the inorganic ion and the organic ion may be a di- or higher valent ion.

4. A polymer functional cured product which is formed by polymerizing and curing the curable composition according to claim 1.

5. The polymer functional cured product according to claim 4,
wherein the polymer functional cured product is an ion-exchange membrane, a proton conductive membrane, a reverse osmosis membrane, a forward osmosis membrane, a polymer electrolyte, or a water-absorbing resin.

6. A polymer functional cured product, comprising:
a polymer having a structural unit represented by the following General Formula (I-1) or (I-2),

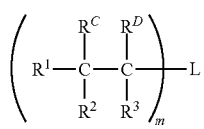

General Formula (I-1)

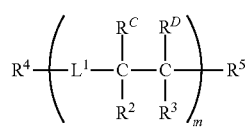

General Formula (I-2)

in General Formulas (I-1) and (I-2), m represents an integer of 2 or greater, and L represents an m-valent group or a single bond; here, in a case where L is a single bond, m is 2; $L^1$ and $L^2$ each independently represent a single bond or a divalent linking group; $R^1$ to $R^5$ each independently represent a hydrogen atom or a substituent, and may be bonded to each other to form a ring, and may be bonded to L, $L^1$, or $L^2$ to form a ring; at least one but not all of $R^C$ and $R^D$ represents a group represented by the following General Formula (a), and the other represents a group represented by the following General Formula (c); and here, m —[C($R^3$)($R^D$)—C($R^1$)($R^2$)($R^C$)]'s may be the same as or different from each other, m -[$L^2$-C($R^3$)($R^D$)—C($R^2$)($R^C$)-$L^1$]-'s may be the same as or different from each other, and in m —[C($R^3$)($R^D$)—C($R^1$)($R^2$)($R^C$)]'s or m -[$L^2$-C($R^3$)($R^D$)—C($R^2$)($R^C$)-$L^1$]-'s, $R^C$ or $R^D$ may be substituted with the group represented by the following General Formula (a); and

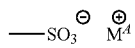

General Formula (a)

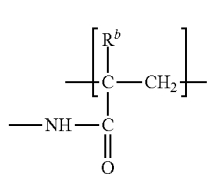

General Formula (c)

in General Formula (a), $M^A$ represents a hydrogen ion, an inorganic ion, or an organic ion; here, each of the inorganic ion and the organic ion may be a di- or higher valent ion; and in General Formula (c), $R^b$ represents a hydrogen atom or an alkyl group.

7. The polymer functional cured product according to claim 6,
wherein m is 2, and L is a single bond, an alkylene group, or an arylene group.

8. The polymer functional cured product according to claim 7,
wherein the structural unit represented by General Formula (I-1) is a structural unit represented by the following General Formula (II), and

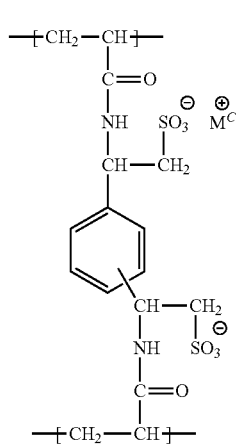

General Formula (II)

in General Formula (II), $M^C$ and $M^D$ each independently represent a hydrogen ion, an inorganic ion, or an organic ion; and here, each of the inorganic ion and the organic ion may be a di- or higher valent ion.

9. A water-soluble multi-acrylamide-containing compound represented by the following General Formula (1-1) or (1-2),

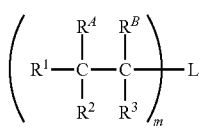

General Formula (1-1)

General Formula (1-2)

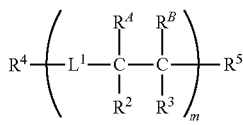

in General Formulas (1-1) and (1-2), m represents an integer of 2 or greater, and L represents an m-valent group or a single bond; here, in a case where L is a single bond, m is 2; $L^1$ and $L^2$ each independently represent a single bond or a divalent linking group; $R^1$ to $R^5$ each independently represent a hydrogen atom or a substituent, and may be bonded to each other to form a ring, and may be bonded to L, $L^1$, or $L^2$ to form a ring; at least one but not all of $R^A$ and $R^B$ represents a group represented by the following General Formula (a), and the other represents a group represented by the following General Formula (b); and here, m —[$C(R^3)(R^B)$—$C(R^1)(R^2)(R^A)$]'s may be the same as or different from each other, m -[$L^2$-$C(R^3)(R^B)$—$C(R^2)(R^A)$-$L^1$]-'s may be the same as or different from each other, and in m —[$C(R^3)(R^B)$—$C(R^1)(R^2)(R^A)$]'s or m -[$L^2$-$C(R^3)(R^B)$—$C(R^2)(R^A)$-$L^1$]-'s, $R^A$ or $R^B$ may be substituted with the group represented by the following General Formula (a); and General Formula (a)

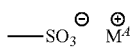

General Formula (b)

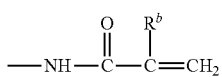

in General Formula (a), $M^A$ represents a hydrogen ion, an inorganic ion, or an organic ion; here, each of the inorganic ion and the organic ion may be a di- or higher valent ion; and in General Formula (b), $R^b$ represents a hydrogen atom or an alkyl group.

10. The water-soluble multi-acrylamide-containing compound according to claim 9,
wherein m is 2, and L is a single bond, an alkylene group, or an arylene group.

11. The water-soluble acrylamide compound according to claim 10,
wherein the water-soluble multi-acrylamide-containing compound represented by General Formula (1-1) is represented by the following General Formula (2), and General Formula (2)

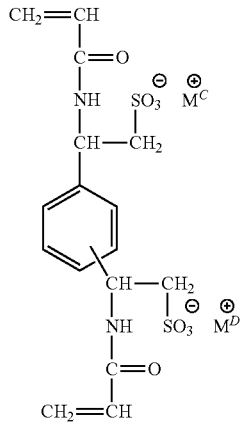

in General Formula (2), $M^C$ and $M^D$ each independently represent a hydrogen ion, an inorganic ion, or an organic ion; and here, each of the inorganic ion and the organic ion may be a di- or higher valent ion.

12. A method for manufacturing the water-soluble multi-acrylamide-containing compound according to claim 9,
wherein an olefin compound represented by the following General Formula (3-1) or (3-2), acrylonitrile, and fuming sulfuric acid are reacted, and General Formula (3-1)

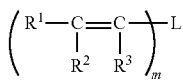

General Formula (3-2)

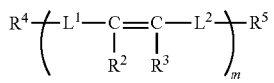

in General Formulas (3-1) and (3-2), m represents an integer of 2 or greater, and L represents an m-valent group or a single bond; here, in a case where L is a single bond, m is 2; $L^1$ and $L^2$ each independently represent a single bond or a divalent linking group; $R^1$ to $R^5$ each independently represent a hydrogen atom or a substituent, and may be bonded to each other to form a ring, and may be bonded to L, $L^1$, or $L^2$ to form a ring; and here, m –[$C(R^3)$=$C(R^1)(R^2)$]'s may be the same as or different from each other, and m –[$L^2$-$C(R^3)$=$C(R^2)$-$L^1$]–'s may be the same as or different from each other.

13. The method for manufacturing a water-soluble multi-acrylamide-containing compound according to claim 12,
wherein m is 2, and L is a single bond, an alkylene group, or an arylene group.

14. The method for manufacturing a water-soluble multi-acrylamide-containing compound according to claim 12,
wherein the olefin compound represented by General Formula (3-1) is divinylbenzene.

* * * * *